(12) United States Patent
Tweden et al.

(10) Patent No.: US 7,008,397 B2
(45) Date of Patent: Mar. 7, 2006

(54) CARDIAC IMPLANT AND METHODS

(75) Inventors: Katherine S. Tweden, Mahtomedi, MN (US); Michael Schollmeyer, Maple Grove, MN (US)

(73) Assignee: Percardia, Inc., Merrimack, NH (US)

( * ) Notice: Subject to any disclaimer, the term of this patent is extended or adjusted under 35 U.S.C. 154(b) by 508 days.

(21) Appl. No.: 10/075,518

(22) Filed: Feb. 13, 2002

(65) Prior Publication Data

US 2003/0158509 A1    Aug. 21, 2003

(51) Int. Cl.
*A61M 5/00* (2006.01)
*A61M 9/22* (2006.01)
*A61F 2/06* (2006.01)

(52) U.S. Cl. .................. 604/8; 604/891.1; 604/6.16; 604/890.1; 623/1.42

(58) Field of Classification Search ............. 604/890.1, 604/8–10, 891.1, 6.16, 65–67; 623/1.3, 1.42, 623/11, 12; 606/194; 128/898
See application file for complete search history.

(56) References Cited

U.S. PATENT DOCUMENTS

| | | | |
|---|---|---|---|
| 4,953,553 A | 9/1990 | Tremulis | |
| 5,193,546 A | 3/1993 | Shaknovich | |
| 5,258,008 A | 11/1993 | Wilk | |
| 5,287,861 A | 2/1994 | Wilk | |

(Continued)

FOREIGN PATENT DOCUMENTS

AU        757647        2/2003

(Continued)

OTHER PUBLICATIONS

Tweden et al. *Ventriculocoronary Artery Bypass (VCAB), a Novel Approach to Myocardial Revascularization*.

(Continued)

*Primary Examiner*—Angela D. Sykes
*Assistant Examiner*—Leslie R. Deak
(74) *Attorney, Agent, or Firm*—Finnegan, Henderson, Farabow, Garrett & Dunner LLP

(57) ABSTRACT

Cardiac implants include a conduit or scaffold having a first therapeutic agent in at least partial covering relation to at least a first portion of the scaffold, and a second therapeutic agent, different from the first therapeutic agent, in at least partial covering relation to at least a second portion of the scaffold. The first therapeutic agent and second therapeutic agent may include one of: antithrombotic agents, anti-inflammatory agents, antiproliferative agents, antibiotic agents, angiogenic agents, antiplatelet agents, anticoagulant agents, rhestenosis preventing agents, hormones and combinations thereof. Methods for making cardiac implants include providing a scaffold, covering at least a first portion of the scaffold with a first therapeutic agent, and covering at least a second portion of the scaffold, different from the first portion, with a second therapeutic agent different from the first therapeutic agent. Methods for treating a patient and for using cardiac implants include forming a blood flow path from a heart chamber directly to the coronary vessel, which includes placing a conduit in a heart wall between the chamber and the vessel with the first end of the conduit protruding into the chamber and protruding beyond an interior surface of the heart wall. The conduit will include a first therapeutic agent in covering relation to at least a first portion of the conduit and a second therapeutic agent in covering relation to at least a second portion.

38 Claims, 5 Drawing Sheets

U.S. PATENT DOCUMENTS

| | | |
|---|---|---|
| 5,330,486 A | 7/1994 | Wilk |
| 5,344,426 A | 9/1994 | Lau et al. |
| 5,389,096 A | 2/1995 | Aita et al. |
| 5,409,019 A | 4/1995 | Wilk |
| 5,429,144 A | 7/1995 | Wilk |
| 5,470,320 A | 11/1995 | Tiefenbrun et al. |
| 5,512,055 A | 4/1996 | Domb et al. |
| 5,554,119 A | 9/1996 | Harrison et al. |
| 5,554,182 A | 9/1996 | Dinh et al. |
| 5,571,166 A | 11/1996 | Dinh et al. |
| 5,578,075 A | 11/1996 | Dayton |
| 5,591,227 A | 1/1997 | Dinh et al. |
| 5,593,434 A | 1/1997 | Williams |
| 5,599,352 A | 2/1997 | Dinh et al. |
| 5,605,696 A | 2/1997 | Eury et al. |
| 5,609,629 A | 3/1997 | Fearnot et al. |
| 5,618,299 A | 4/1997 | Khosravi et al. |
| 5,624,411 A | 4/1997 | Tuch |
| 5,662,124 A | 9/1997 | Wilk |
| 5,674,276 A * | 10/1997 | Andersen et al. ............. 623/1.5 |
| 5,679,400 A | 10/1997 | Tuch |
| 5,697,967 A | 12/1997 | Dinh et al. |
| 5,707,385 A | 1/1998 | Williams |
| 5,733,267 A | 3/1998 | Del Toro |
| 5,733,327 A | 3/1998 | Igaki et al. |
| 5,755,682 A | 5/1998 | Knudson et al. |
| 5,758,663 A | 6/1998 | Wilk et al. |
| 5,776,184 A | 7/1998 | Tuch |
| 5,783,454 A | 7/1998 | Spallholz et al. |
| 5,788,979 A | 8/1998 | Alt et al. |
| 5,807,384 A | 9/1998 | Mueller |
| 5,810,836 A | 9/1998 | Hussein et al. |
| 5,824,071 A | 10/1998 | Nelson et al. |
| 5,830,222 A | 11/1998 | Makower |
| 5,830,883 A | 11/1998 | Block et al. |
| 5,837,008 A | 11/1998 | Berg et al. |
| 5,851,231 A * | 12/1998 | Wolff et al. ................ 623/1.42 |
| 5,873,904 A | 2/1999 | Ragheb et al. |
| 5,876,373 A | 3/1999 | Giba et al. |
| 5,876,433 A | 3/1999 | Lunn |
| 5,878,751 A | 3/1999 | Hussein et al. |
| 5,885,259 A | 3/1999 | Berg |
| 5,908,028 A | 6/1999 | Wilk |
| 5,908,029 A | 6/1999 | Knudson et al. |
| 5,922,022 A | 7/1999 | Nash et al. |
| 5,925,012 A | 7/1999 | Murphy-Chutorian et al. |
| 5,931,848 A | 8/1999 | Saadat |
| 5,935,161 A | 8/1999 | Robinson et al. |
| 5,938,632 A | 8/1999 | Ellis |
| 5,944,019 A | 8/1999 | Knudson et al. |
| 5,968,064 A | 10/1999 | Selmon et al. |
| 5,971,993 A | 10/1999 | Hussein et al. |
| 5,972,027 A | 10/1999 | Johnson |
| 5,976,155 A | 11/1999 | Foreman et al. |
| 5,980,533 A | 11/1999 | Holman |
| 5,980,548 A | 11/1999 | Evans et al. |
| 5,980,566 A | 11/1999 | Alt et al. |
| 5,980,972 A | 11/1999 | Ding |
| 5,984,956 A | 11/1999 | Tweden et al. |
| 5,994,151 A | 11/1999 | Spallholz et al. |
| 5,997,525 A | 12/1999 | March et al. |
| 5,999,678 A | 12/1999 | Murphy-Chutorian et al. |
| 6,004,261 A | 12/1999 | Sinofsky et al. |
| 6,004,347 A | 12/1999 | McNamara et al. |
| 6,007,543 A | 12/1999 | Ellis et al. |
| 6,010,449 A | 1/2000 | Selmon et al. |
| 6,026,814 A | 2/2000 | LaFontaine et al. |
| 6,029,672 A | 2/2000 | Vanney et al. |
| 6,033,917 A | 3/2000 | Spallholz et al. |
| 6,035,856 A | 3/2000 | LaFontaine et al. |
| 6,036,677 A | 3/2000 | Javier, Jr. et al. |
| 6,036,697 A | 3/2000 | DiCaprio |
| 6,040,197 A | 3/2000 | Spallholz et al. |
| 6,043,098 A | 3/2000 | Spallholz et al. |
| 6,043,099 A | 3/2000 | Spallholz et al. |
| 6,045,565 A | 4/2000 | Ellis et al. |
| 6,053,924 A | 4/2000 | Hussein |
| 6,053,942 A | 4/2000 | Eno et al. |
| 6,056,743 A | 5/2000 | Ellis et al. |
| 6,067,988 A | 5/2000 | Mueller |
| 6,068,638 A | 5/2000 | Makower |
| 6,071,292 A | 6/2000 | Makower et al. |
| 6,076,529 A | 6/2000 | Vanney et al. |
| 6,077,714 A | 6/2000 | Spallholz et al. |
| 6,080,163 A | 6/2000 | Hussein et al. |
| 6,080,170 A | 6/2000 | Nash et al. |
| 6,092,526 A | 7/2000 | LaFontaine et al. |
| 6,093,166 A | 7/2000 | Knudson et al. |
| 6,093,177 A | 7/2000 | Javier, Jr. et al. |
| 6,093,185 A | 7/2000 | Ellis et al. |
| 6,102,941 A | 8/2000 | Tweden et al. |
| 6,113,630 A | 9/2000 | Vanney et al. |
| 6,113,823 A | 9/2000 | Eno |
| 6,120,520 A | 9/2000 | Saadat et al. |
| 6,120,536 A | 9/2000 | Ding et al. |
| 6,123,682 A | 9/2000 | Knudson et al. |
| 6,126,649 A | 10/2000 | VanTassel et al. |
| 6,126,654 A | 10/2000 | Giba et al. |
| 6,132,451 A | 10/2000 | Payne et al. |
| 6,139,541 A | 10/2000 | Vanney et al. |
| 6,155,264 A | 12/2000 | Ressemann et al. |
| 6,156,031 A | 12/2000 | Aita et al. |
| 6,157,852 A | 12/2000 | Selmon et al. |
| 6,159,225 A | 12/2000 | Makower |
| 6,165,185 A | 12/2000 | Shennib et al. |
| 6,165,188 A | 12/2000 | Saadat et al. |
| 6,171,251 B1 | 1/2001 | Mueller et al. |
| 6,182,668 B1 | 2/2001 | Tweden et al. |
| 6,186,972 B1 | 2/2001 | Nelson et al. |
| 6,190,353 B1 | 2/2001 | Makower et al. |
| 6,193,726 B1 | 2/2001 | Vanney |
| 6,193,734 B1 | 2/2001 | Bolduc et al. |
| 6,196,230 B1 | 3/2001 | Hall et al. |
| 6,197,050 B1 | 3/2001 | Eno et al. |
| 6,197,324 B1 | 3/2001 | Crittenden |
| 6,200,311 B1 | 3/2001 | Danek et al. |
| 6,203,556 B1 | 3/2001 | Evans et al. |
| 6,206,914 B1 * | 3/2001 | Soykan et al. ............. 623/1.42 |
| 6,206,915 B1 | 3/2001 | Fagan et al. |
| 6,213,126 B1 | 4/2001 | LaFontaine et al. |
| 6,214,041 B1 | 4/2001 | Tweden et al. |
| 6,217,527 B1 | 4/2001 | Selmon et al. |
| 6,217,549 B1 | 4/2001 | Selmon et al. |
| 6,217,575 B1 | 4/2001 | DeVore et al. |
| 6,221,049 B1 | 4/2001 | Selmon et al. |
| 6,223,752 B1 | 5/2001 | Vanney et al. |
| 6,224,584 B1 | 5/2001 | March et al. |
| 6,231,546 B1 | 5/2001 | Milo et al. |
| 6,231,551 B1 | 5/2001 | Barbut |
| 6,231,587 B1 | 5/2001 | Makower |
| 6,231,600 B1 | 5/2001 | Zhong |
| 6,235,000 B1 | 5/2001 | Milo et al. |
| 6,237,607 B1 | 5/2001 | Vanney et al. |
| 6,238,406 B1 | 5/2001 | Ellis et al. |
| 6,241,667 B1 | 6/2001 | Vetter et al. |
| 6,248,112 B1 | 6/2001 | Gambale et al. |
| 6,250,305 B1 | 6/2001 | Tweden |
| 6,251,079 B1 | 6/2001 | Gambale et al. |
| 6,251,104 B1 | 6/2001 | Kesten et al. |
| 6,251,116 B1 | 6/2001 | Shennib et al. |
| 6,251,418 B1 | 6/2001 | Ahern et al. |
| 6,253,443 B1 | 7/2001 | Johnson |
| 6,253,768 B1 | 7/2001 | Wilk |
| 6,253,769 B1 | 7/2001 | LaFontaine et al. |

| Patent No. | Date | Inventor |
|---|---|---|
| 6,254,564 B1 | 7/2001 | Wilk et al. |
| 6,258,052 B1 | 7/2001 | Milo |
| 6,258,119 B1 | 7/2001 | Hussein et al. |
| 6,261,304 B1 | 7/2001 | Hall et al. |
| 6,283,951 B1 | 9/2001 | Flaherty et al. |
| 6,283,983 B1 | 9/2001 | Makower et al. |
| 6,285,903 B1 | 9/2001 | Rosenthal et al. |
| 6,287,317 B1 | 9/2001 | Makower et al. |
| 6,290,709 B1 | 9/2001 | Ellis et al. |
| 6,290,728 B1 | 9/2001 | Phelps et al. |
| 6,302,875 B1 | 10/2001 | Makower et al. |
| 6,302,892 B1 | 10/2001 | Wilk |
| 6,322,548 B1 | 11/2001 | Payne et al. |
| 6,330,884 B1 | 12/2001 | Kim |
| 6,344,027 B1 | 2/2002 | Goll |
| 6,350,248 B1 | 2/2002 | Knudson et al. |
| 6,352,543 B1 | 3/2002 | Cole |
| 6,361,519 B1 | 3/2002 | Knudson et al. |
| 6,363,938 B1 | 4/2002 | Saadat et al. |
| 6,363,939 B1 | 4/2002 | Wilk |
| 6,375,615 B1 | 4/2002 | Flaherty et al. |
| 6,379,319 B1 | 4/2002 | Garibotto et al. |
| 6,387,119 B1 | 5/2002 | Wolf et al. |
| 6,390,098 B1 | 5/2002 | LaFontaine et al. |
| 6,395,208 B1 | 5/2002 | Herweck et al. |
| 6,402,740 B1 | 6/2002 | Ellis et al. |
| 6,406,488 B1 | 6/2002 | Tweden et al. |
| 6,406,491 B1 | 6/2002 | Vanney |
| 6,409,697 B1 | 6/2002 | Eno et al. |
| 6,409,751 B1 | 6/2002 | Hall et al. |
| 6,416,490 B1 | 7/2002 | Ellis et al. |
| 6,423,089 B1 | 7/2002 | Gingras et al. |
| 6,432,119 B1 | 8/2002 | Saadat |
| 6,432,126 B1 | 8/2002 | Gambale et al. |
| 6,432,127 B1 | 8/2002 | Kim et al. |
| 6,432,132 B1 | 8/2002 | Cottone et al. |
| 6,443,158 B1 | 9/2002 | LaFontaine et al. |
| 6,447,522 B1 | 9/2002 | Gambale et al. |
| 6,447,539 B1 | 9/2002 | Nelson et al. |
| 6,454,760 B1 | 9/2002 | Vanney |
| 6,454,794 B1 | 9/2002 | Knudson et al. |
| 6,458,092 B1 | 10/2002 | Gambale et al. |
| 6,458,140 B1 | 10/2002 | Akin et al. |
| 6,458,323 B1 | 10/2002 | Boekstegers |
| 6,464,709 B1 | 10/2002 | Shennib et al. |
| 6,475,226 B1 | 11/2002 | Belef et al. |
| 6,475,244 B1 | 11/2002 | Herweck et al. |
| 6,482,220 B1 | 11/2002 | Mueller |
| 6,491,689 B1 | 12/2002 | Ellis et al. |
| 6,491,707 B1 | 12/2002 | Makower et al. |
| 6,506,408 B1 | 1/2003 | Palasis |
| 6,508,783 B1 | 1/2003 | DeVore |
| 6,508,824 B1 | 1/2003 | Flaherty et al. |
| 6,508,825 B1 | 1/2003 | Selmon et al. |
| 6,511,458 B1 | 1/2003 | Milo et al. |
| 6,514,217 B1 | 2/2003 | Selmon et al. |
| 6,514,271 B1 | 2/2003 | Evans et al. |
| 6,517,527 B1 | 2/2003 | Gambale et al. |
| 6,517,558 B1 | 2/2003 | Gittings et al. |
| 6,524,323 B1 | 2/2003 | Nash et al. |
| 6,524,324 B1 | 2/2003 | Mueller et al. |
| 6,530,914 B1 | 3/2003 | Mickley |
| 6,533,779 B1 | 3/2003 | Kinsella et al. |
| 6,544,220 B1 | 4/2003 | Shuman et al. |
| 6,544,230 B1 | 4/2003 | Flaherty |
| 6,559,132 B1 | 5/2003 | Holmer |
| 6,561,998 B1 | 5/2003 | Roth et al. |
| 6,562,066 B1 | 5/2003 | Martin |
| 6,565,528 B1 | 5/2003 | Mueller |
| 6,565,594 B1 | 5/2003 | Herweck et al. |
| 6,569,145 B1 | 5/2003 | Shmulewitz et al. |
| 6,569,147 B1 | 5/2003 | Evans et al. |
| 6,573,311 B1 | 6/2003 | Martakos et al. |
| 6,575,168 B1 | 6/2003 | LaFontaine et al. |
| 6,579,311 B1 | 6/2003 | Makower |
| 6,582,444 B1 * | 6/2003 | Wilk .......................... 606/153 |
| 6,582,463 B1 | 6/2003 | Mowry et al. |
| 6,585,650 B1 | 7/2003 | Solem |
| 6,587,718 B1 | 7/2003 | Talpade |
| 6,589,164 B1 | 7/2003 | Flaherty |
| 6,599,304 B1 | 7/2003 | Selmon et al. |
| 6,602,241 B1 | 8/2003 | Makower et al. |
| 6,605,053 B1 * | 8/2003 | Kamm et al. .................. 604/8 |
| 6,605,113 B1 | 8/2003 | Wilk |
| 6,610,100 B1 | 8/2003 | Phelps et al. |
| 6,613,026 B1 | 9/2003 | Palasis et al. |
| 6,613,081 B1 | 9/2003 | Kim et al. |
| 6,616,626 B1 | 9/2003 | Crank et al. |
| 6,616,675 B1 | 9/2003 | Evard et al. |
| 6,632,470 B1 | 10/2003 | Morra et al. |
| 6,635,214 B1 | 10/2003 | Rapacki et al. |
| 6,638,237 B1 | 10/2003 | Guiles et al. |
| 6,638,247 B1 | 10/2003 | Selmon et al. |
| 6,638,293 B1 | 10/2003 | Makower et al. |
| 6,641,610 B1 | 11/2003 | Briefs et al. |
| 6,651,670 B1 | 11/2003 | Rapacki et al. |
| 6,652,540 B1 | 11/2003 | Cole et al. |
| 6,652,546 B1 | 11/2003 | Nash et al. |
| 6,655,386 B1 | 12/2003 | Makower et al. |
| 6,660,003 B1 | 12/2003 | DeVore et al. |
| 6,660,024 B1 | 12/2003 | Flaherty et al. |
| 6,666,863 B1 | 12/2003 | Wentzel et al. |
| 6,669,691 B1 | 12/2003 | Taimisto |
| 6,669,709 B1 | 12/2003 | Cohn et al. |
| 6,676,695 B1 | 1/2004 | Solem |
| 6,685,648 B1 | 2/2004 | Flaherty et al. |
| 6,685,716 B1 | 2/2004 | Flaherty et al. |
| 6,694,983 B1 | 2/2004 | Wolf et al. |
| 6,709,425 B1 | 3/2004 | Gambale et al. |
| 6,709,427 B1 | 3/2004 | Nash et al. |
| 6,709,444 B1 | 3/2004 | Makower |
| 6,719,770 B1 | 4/2004 | Laufer et al. |
| 6,726,677 B1 | 4/2004 | Flaherty et al. |
| 6,746,426 B1 | 6/2004 | Flaherty et al. |
| 6,746,464 B1 | 6/2004 | Makower |
| 6,748,258 B1 | 6/2004 | Mueller et al. |
| 2001/0000041 A1 | 3/2001 | Selmon et al. |
| 2001/0003985 A1 | 6/2001 | LaFontaine et al. |
| 2001/0004683 A1 | 6/2001 | Gambale et al. |
| 2001/0004690 A1 | 6/2001 | Gambale et al. |
| 2001/0004699 A1 | 6/2001 | Gittings et al. |
| 2001/0008969 A1 | 7/2001 | Evans et al. |
| 2001/0012924 A1 | 8/2001 | Milo et al. |
| 2001/0012948 A1 | 8/2001 | Vanney |
| 2001/0014813 A1 | 8/2001 | Saadat et al. |
| 2001/0016700 A1 | 8/2001 | Eno et al. |
| 2001/0018596 A1 | 8/2001 | Selmon et al. |
| 2001/0020172 A1 | 9/2001 | Selmon et al. |
| 2001/0025643 A1 | 10/2001 | Foley |
| 2001/0027287 A1 | 10/2001 | Shmulewitz et al. |
| 2001/0029385 A1 | 10/2001 | Shennib et al. |
| 2001/0034547 A1 | 10/2001 | Hall et al. |
| 2001/0037117 A1 | 11/2001 | Gambale et al. |
| 2001/0037149 A1 | 11/2001 | Wilk |
| 2001/0039426 A1 | 11/2001 | Makower et al. |
| 2001/0039445 A1 | 11/2001 | Hall et al. |
| 2001/0041902 A1 | 11/2001 | Lepulu et al. |
| 2001/0044631 A1 | 11/2001 | Akin et al. |
| 2001/0047165 A1 | 11/2001 | Makower et al. |
| 2001/0047197 A1 | 11/2001 | Foley |
| 2001/0049523 A1 | 12/2001 | DeVore et al. |
| 2001/0053932 A1 | 12/2001 | Phelps et al. |
| 2002/0002349 A1 | 1/2002 | Flaherty et al. |
| 2002/0004662 A1 | 1/2002 | Wilk |
| 2002/0004663 A1 | 1/2002 | Gittings et al. |
| 2002/0007138 A1 | 1/2002 | Wilk et al. |

| | | |
|---|---|---|
| 2002/0029079 A1 | 3/2002 | Kim et al. |
| 2002/0032476 A1 | 3/2002 | Gambale et al. |
| 2002/0032478 A1 | 3/2002 | Boekstegers et al. |
| 2002/0033180 A1 | 3/2002 | Solem |
| 2002/0045928 A1 | 4/2002 | Boekstegers |
| 2002/0049486 A1 | 4/2002 | Knudson et al. |
| 2002/0049495 A1 | 4/2002 | Kutryk et al. |
| 2002/0058897 A1 | 5/2002 | Renati |
| 2002/0062146 A1 | 5/2002 | Makower et al. |
| 2002/0065478 A1 | 5/2002 | Knudson et al. |
| 2002/0072699 A1 | 6/2002 | Knudson et al. |
| 2002/0072758 A1 | 6/2002 | Reo et al. |
| 2002/0077566 A1 | 6/2002 | Laroya et al. |
| 2002/0077654 A1 | 6/2002 | Javier, Jr. et al. |
| 2002/0082546 A1 | 6/2002 | Crank et al. |
| 2002/0092535 A1 | 7/2002 | Wilk |
| 2002/0092536 A1 | 7/2002 | LaFontaine et al. |
| 2002/0095110 A1 | 7/2002 | Vanney et al. |
| 2002/0095111 A1 | 7/2002 | Tweden et al. |
| 2002/0095206 A1 | 7/2002 | Addonizio et al. |
| 2002/0099392 A1 | 7/2002 | Mowry et al. |
| 2002/0099404 A1 | 7/2002 | Mowry |
| 2002/0100484 A1 | 8/2002 | Hall et al. |
| 2002/0103459 A1 | 8/2002 | Sparks et al. |
| 2002/0103495 A1 | 8/2002 | Cole |
| 2002/0103534 A1 | 8/2002 | Vanney et al. |
| 2002/0111644 A1 | 8/2002 | Shuman et al. |
| 2002/0111672 A1 | 8/2002 | Kim et al. |
| 2002/0123698 A1 | 9/2002 | Garibotto et al. |
| 2002/0123786 A1 | 9/2002 | Gittings et al. |
| 2002/0138087 A1 | 9/2002 | Shennib et al. |
| 2002/0143285 A1 | 10/2002 | Eno et al. |
| 2002/0143289 A1 | 10/2002 | Ellis et al. |
| 2002/0143347 A1 | 10/2002 | Cole et al. |
| 2002/0144696 A1 | 10/2002 | Sharkawy et al. |
| 2002/0161383 A1 | 10/2002 | Akin et al. |
| 2002/0161424 A1 | 10/2002 | Rapacki et al. |
| 2002/0165479 A1 | 11/2002 | Wilk |
| 2002/0165606 A1 | 11/2002 | Wolf et al. |
| 2002/0179098 A1 | 12/2002 | Makower et al. |
| 2002/0183716 A1 | 12/2002 | Herweck et al. |
| 2002/0193782 A1 | 12/2002 | Ellis et al. |
| 2003/0015816 A1 | 1/2003 | Rapacki et al. |
| 2003/0018379 A1 | 1/2003 | Knudson et al. |
| 2003/0044315 A1 | 3/2003 | Boekstegers |
| 2003/0045828 A1 | 3/2003 | Wilk |
| 2003/0055371 A1 | 3/2003 | Wolf et al. |
| 2003/0062650 A1 | 4/2003 | Martakos et al. |
| 2003/0069532 A1 | 4/2003 | Mowry et al. |
| 2003/0069587 A1 | 4/2003 | Schorgi et al. |
| 2003/0073973 A1 | 4/2003 | Evans et al. |
| 2003/0074006 A1 | 4/2003 | Mowry et al. |
| 2003/0078561 A1 | 4/2003 | Gambale et al. |
| 2003/0078562 A1 | 4/2003 | Makower et al. |
| 2003/0083678 A1 | 5/2003 | Herweck et al. |
| 2003/0097172 A1 | 5/2003 | Shalev et al. |
| 2003/0100920 A1 | 5/2003 | Akin et al. |
| 2003/0105514 A1 | 6/2003 | Phelps et al. |
| 2003/0114872 A1 | 6/2003 | Mueller et al. |
| 2003/0120195 A1 | 6/2003 | Milo et al. |
| 2003/0120259 A1 | 6/2003 | Mickley |
| 2003/0125798 A1 | 7/2003 | Martin |
| 2003/0130611 A1 | 7/2003 | Martin |
| 2003/0130719 A1 | 7/2003 | Martin |
| 2003/0135260 A1 | 7/2003 | Kohler et al. |
| 2003/0149474 A1 | 8/2003 | Becker |
| 2003/0153901 A1 | 8/2003 | Herweck et al. |
| 2003/0158573 A1 | 8/2003 | Gittings et al. |
| 2003/0163198 A1 | 8/2003 | Morra et al. |
| 2003/0171800 A1 | 9/2003 | Bicek et al. |
| 2003/0181938 A1 | 9/2003 | Roth et al. |
| 2003/0191449 A1 | 10/2003 | Nash et al. |
| 2003/0195457 A1 | 10/2003 | LaFontaine et al. |
| 2003/0195458 A1 | 10/2003 | Phelps et al. |
| 2003/0195606 A1 | 10/2003 | Davidson et al. |
| 2003/0204160 A1 | 10/2003 | Kamm et al. |
| 2003/0212413 A1 | 11/2003 | Wilk |
| 2003/0216678 A1 | 11/2003 | March et al. |
| 2003/0216679 A1 | 11/2003 | Wolf et al. |
| 2003/0229366 A1 | 12/2003 | Reggie et al. |
| 2003/0236542 A1 | 12/2003 | Makower |
| 2004/0006298 A1 | 1/2004 | Wilk |
| 2004/0006301 A1 | 1/2004 | Sell et al. |
| 2004/0015225 A1 | 1/2004 | Kim et al. |
| 2004/0019348 A1 | 1/2004 | Stevens et al. |
| 2004/0037946 A1 | 2/2004 | Morra et al. |
| 2004/0044392 A1 | 3/2004 | Von Oepen |
| 2004/0059280 A1 | 3/2004 | Makower et al. |
| 2004/0073157 A1 | 4/2004 | Knudson et al. |
| 2004/0073238 A1 | 4/2004 | Makower |
| 2004/0077987 A1 | 4/2004 | Rapacki et al. |
| 2004/0077988 A1 | 4/2004 | Tweden et al. |
| 2004/0077990 A1 | 4/2004 | Knudson et al. |
| 2004/0088042 A1 | 5/2004 | Kim et al. |
| 2004/0106931 A1 | 6/2004 | Guiles et al. |
| 2004/0113306 A1 | 6/2004 | Rapacki et al. |
| 2004/0118415 A1 | 6/2004 | Hall et al. |
| 2004/0122318 A1 | 6/2004 | Flaherty et al. |
| 2004/0122347 A1 | 6/2004 | Knudson et al. |
| 2004/0133154 A1 | 7/2004 | Flaherty et al. |
| 2004/0133225 A1 | 7/2004 | Makower |

FOREIGN PATENT DOCUMENTS

| | | |
|---|---|---|
| EP | 0 732 088 A2 | 9/1996 |
| EP | 0 815 798 A2 | 7/1997 |
| EP | 0 829 239 A1 | 8/1997 |
| EP | 0 792 624 A1 | 9/1997 |
| EP | 0 797 957 A1 | 10/1997 |
| EP | 0 797 958 A1 | 10/1997 |
| EP | 0 799 604 A1 | 10/1997 |
| EP | 0 801 928 A1 | 10/1997 |
| EP | 0 836 834 A2 | 10/1997 |
| EP | 0 876 796 A2 | 5/1998 |
| EP | 0 853 921 A2 | 7/1998 |
| EP | 0 858 779 A1 | 8/1998 |
| EP | 0 876 803 A2 | 11/1998 |
| EP | 0 888 750 A1 | 1/1999 |
| EP | 0 895 752 A1 | 2/1999 |
| EP | 0 934 728 A2 | 8/1999 |
| EP | 1 020 166 A1 | 7/2000 |
| EP | 1 027 870 A1 | 8/2000 |
| EP | 1 088 564 A1 | 4/2001 |
| EP | 1 097 676 A1 | 5/2001 |
| EP | 1 166 721 A2 | 1/2002 |
| EP | 0 959 815 A1 | 12/2002 |
| EP | 1 112 097 A1 | 6/2003 |
| GB | 2 316 322 B | 2/1998 |
| WO | WO 96/32972 | 10/1996 |
| WO | WO 96/35469 | 11/1996 |
| WO | WO 96/39962 | 12/1996 |
| WO | WO 96/39964 | 12/1996 |
| WO | WO 96/39965 | 12/1996 |
| WO | WO 97/13463 | 4/1997 |
| WO | WO 97/13471 | 4/1997 |
| WO | WO 97/27893 | 8/1997 |
| WO | WO 97/27897 | 8/1997 |
| WO | WO 97/27898 | 8/1997 |
| WO | WO 97/32551 | 9/1997 |
| WO | WO 97/43961 | 11/1997 |
| WO | WO 98/03118 | 1/1998 |
| WO | WO 98/06356 | 2/1998 |
| WO | WO 98/10714 | 3/1998 |
| WO | WO 98/16161 | 4/1998 |
| WO | WO 98/24373 | 6/1998 |
| WO | WO 98/25533 | 6/1998 |

| | | |
|---|---|---|
| WO | WO 98/38916 | 9/1998 |
| WO | WO 98/38925 | 9/1998 |
| WO | WO 98/38939 | 9/1998 |
| WO | WO 98/38941 | 9/1998 |
| WO | WO 98/39038 | 9/1998 |
| WO | WO 98/46115 | 10/1998 |
| WO | WO 98/46119 | 10/1998 |
| WO | WO 98/49964 | 11/1998 |
| WO | WO 98/57590 | 12/1998 |
| WO | WO 98/57591 | 12/1998 |
| WO | WO 98/57592 | 12/1998 |
| WO | WO 99/07296 | 2/1999 |
| WO | WO 99/08624 | 2/1999 |
| WO | WO 99/15220 | 4/1999 |
| WO | WO 99/17671 | 4/1999 |
| WO | WO 99/17683 | 4/1999 |
| WO | WO 99/21490 | 5/1999 |
| WO | WO 99/21510 | 5/1999 |
| WO | WO 99/22655 | 5/1999 |
| WO | WO 99/22658 | 5/1999 |
| WO | WO 99/25273 | 5/1999 |
| WO | WO 99/27985 | 6/1999 |
| WO | WO 99/35977 | 7/1999 |
| WO | WO 99/35979 | 7/1999 |
| WO | WO 99/35980 | 7/1999 |
| WO | WO 99/36000 | 7/1999 |
| WO | WO 99/36001 | 7/1999 |
| WO | WO 99/38459 | 8/1999 |
| WO | WO 99/40853 | 8/1999 |
| WO | WO 99/40868 | 8/1999 |
| WO | WO 99/40963 | 8/1999 |
| WO | WO 99/44524 | 9/1999 |
| WO | WO 99/48545 | 9/1999 |
| WO | WO 99/48549 | 9/1999 |
| WO | WO 99/49793 | 10/1999 |
| WO | WO 99/49910 | 10/1999 |
| WO | WO 99/51162 | 10/1999 |
| WO | WO 99/53863 | 10/1999 |
| WO | WO 99/55406 | 11/1999 |
| WO | WO 99/60941 | 12/1999 |
| WO | WO 99/62430 | 12/1999 |
| WO | WO 00/09195 | 2/2000 |
| WO | WO 00/12029 | 3/2000 |
| WO | WO 00/13722 | 3/2000 |
| WO | WO 00/15146 | 3/2000 |
| WO | WO 00/15147 | 3/2000 |
| WO | WO 00/15148 | 3/2000 |
| WO | WO 00/15149 A1 | 3/2000 |
| WO | WO 00/15275 | 3/2000 |
| WO | WO 00/18302 | 4/2000 |
| WO | WO 00/18323 | 4/2000 |
| WO | WO 00/18325 | 4/2000 |
| WO | WO 00/18326 | 4/2000 |
| WO | WO 00/18331 | 4/2000 |
| WO | WO 00/18462 | 4/2000 |
| WO | WO 00/21436 | 4/2000 |
| WO | WO 00/21461 | 4/2000 |
| WO | WO 00/21463 | 4/2000 |
| WO | WO 00/24449 | 5/2000 |
| WO | WO 00/33725 | 6/2000 |
| WO | WO 00/35376 | 6/2000 |
| WO | WO 00/36997 | 6/2000 |
| WO | WO 00/41632 | 7/2000 |
| WO | WO 00/41633 | 7/2000 |
| WO | WO 00/43051 | 7/2000 |
| WO | WO 00/45711 | 8/2000 |
| WO | WO 00/45886 | 8/2000 |
| WO | WO 00/49952 | 8/2000 |
| WO | WO 00/49954 | 8/2000 |
| WO | WO 00/49956 | 8/2000 |
| WO | WO 00/54660 | 9/2000 |
| WO | WO 00/54661 | 9/2000 |
| WO | WO 00/56224 | 9/2000 |
| WO | WO 00/56225 | 9/2000 |
| WO | WO 00/56387 | 9/2000 |
| WO | WO 00/66007 | 11/2000 |
| WO | WO 00/66009 | 11/2000 |
| WO | WO 00/66035 | 11/2000 |
| WO | WO 00/69345 | 11/2000 |
| WO | WO 00/69504 | 11/2000 |
| WO | WO 00/71195 A1 | 11/2000 |
| WO | WO 01/08566 A1 | 2/2001 |
| WO | WO 01/08602 A1 | 2/2001 |
| WO | WO 01/10340 A1 | 2/2001 |
| WO | WO 01/10341 A2 | 2/2001 |
| WO | WO 01/10347 A1 | 2/2001 |
| WO | WO 01/10348 A1 | 2/2001 |
| WO | WO 01/10349 A1 | 2/2001 |
| WO | WO 01/10350 A1 | 2/2001 |
| WO | WO 01/17440 A1 | 3/2001 |
| WO | WO 01/17456 A1 | 3/2001 |
| WO | WO 01/23016 A1 | 4/2001 |
| WO | WO 01/41657 A1 | 6/2001 |
| WO | WO 01/49187 A1 | 7/2001 |
| WO | WO 01/68158 A1 | 9/2001 |
| WO | WO 01/70133 A2 | 9/2001 |
| WO | WO 01/72239 A2 | 10/2001 |
| WO | WO 01/78801 A2 | 10/2001 |
| WO | WO 01/82803 A1 | 11/2001 |
| WO | WO 01/82837 A2 | 11/2001 |
| WO | WO 02/011647 A2 | 2/2002 |
| WO | WO 02/011807 A2 | 2/2002 |
| WO | WO 02/013698 A1 | 2/2002 |
| WO | WO 02/013699 A1 | 2/2002 |
| WO | WO 02/013703 A1 | 2/2002 |
| WO | WO 02/013704 A1 | 2/2002 |
| WO | WO 02/024108 A2 | 3/2002 |
| WO | WO 02/024247 A1 | 3/2002 |
| WO | WO 02/024248 A2 | 3/2002 |
| WO | WO 02/026310 A1 | 4/2002 |
| WO | WO 02/026462 A1 | 4/2002 |
| WO | WO 02/030325 A2 | 4/2002 |
| WO | WO 02/030326 A2 | 4/2002 |
| WO | WO 02/030330 A2 | 4/2002 |
| WO | WO 02/032330 A2 | 4/2002 |
| WO | WO 02/034323 A2 | 5/2002 |
| WO | WO 02/045598 A2 | 6/2002 |
| WO | WO 02/049465 A2 | 6/2002 |
| WO | WO 02/056937 A2 | 7/2002 |
| WO | WO 02/058567 A2 | 8/2002 |
| WO | WO 02/058591 A2 | 8/2002 |
| WO | WO 02/060509 A1 | 8/2002 |
| WO | WO 02/062265 A2 | 8/2002 |
| WO | WO 02/064020 A2 | 8/2002 |
| WO | WO 02/071974 A2 | 9/2002 |
| WO | WO 02/074175 A2 | 9/2002 |
| WO | WO 02/091958 A1 | 11/2002 |
| WO | WO 03/008005 A2 | 1/2003 |
| WO | WO 03/015638 A2 | 2/2003 |
| WO | WO 03/017870 A1 | 3/2003 |
| WO | WO 03/024307 A2 | 3/2003 |
| WO | WO 03/028522 A2 | 4/2003 |
| WO | WO 03/030744 A1 | 4/2003 |
| WO | WO 03/030784 A1 | 4/2003 |
| WO | WO 03/041469 A2 | 6/2003 |

OTHER PUBLICATIONS

Wakabayashi et al.; *Myocardial boring for the ischemic heart*; International Cardiovasvular Society; vol. 95 (Nov. 1967) pp. 743-752.

Lary et al.; *Myocardial revascularization using the epicardium*; Arch. Surg., vol. 98 (Jan. 1969) pp. 69-72.

Kuzela et al.; *Experimental evaluation of direct transventricular revascularization*; Journal of Thoracic and Cardiovascular Surgery, vol. 57 (Jan.-Jun. 1969) pp. 770-773.

Anabtawi et al.; *Experimental evaluation of myocardial tunnelization as a method of myocardial revascularization*; Journal of Thoracic and Cardiovascular Surgery, (Nov. 1969) pp. 638-646.

Palmaz et al.; *Expandable intrahepatic portacaval shunt stents in dogs with chronic portal hypertension*; AJR, vol. 147 (Dec. 1986) pp. 1251-1254.

Palmaz et al.; *Expandable intrahepatic portacaval shunt stents: early epxerience in the dog*; AJR, vol. 145 (Oct. 1985) pp. 821-825.

Gardner et al.; *An experimental anatomic study of indirect myocardial revascularization*; Journal of Surgical Research, vol. 11 (1971) pp. 243-247.

Lary et al., *A method for creating a coronary-myocardial artery*; Surgery, vol. 59 (Jun. 1966) pp. 1061-10640.

Ahmed et al.; *Silent left coronary artery-cameral fistula: probable cause of myocardial ischemia*; American Heart Journal, vol. 104 (Oct. 1982) pp. 869-870.

Zemel et al.; *Percutaneous transjugular portosystemic shunt*; JAMA, vol. 266 (Jul. 1991) pp. 390-393.

Richter et al.; *Transjugular intrahepatic portacaval stent shunt: preliminary clinical results*; RSNA-SCVIR, vol. 174 (Mar. 1990) pp. 1027-1030.

Angell et al., *Organ viability with hypothermia*, The Journal of Thoracic and Cardiovascular Surgery, vol. 58, No. 5 (Nov. 1969), pp. 619-646.

Massimo et al., Myocardial, *Revascularization by a New Method of Carrying Blood Directly from the left ventricular cavity into the Coronary Circulation*, from the S. Maria. Nuova Hospital: Surgeon-in-Chief, Tominiaso Greco, M.D., received for publication Oct. 16, 1956, J. Thoracic Surgery vol. 34: (1957) pp. 257-264.

Archie, Joseph P. Jr., *Intramyocardial Pressure: Effect of Preload on Transmural Distribution of Systolic Coronary Blood Flow*; The American Journal of Cardiology, vol. 35, (Jun. 1975), pp. 904-911.

Burch, et al., An International Publication for the Study of the Circulation, American Heart Journal, (Jan. 1980), pp. 8-9.

Lee et al., *Effects of laser Irradiation delivered by flexible fiberoptic system on the left ventricular internal myocardium*, AMJ, (Sep. 1983), vol. 106, No. 3, pp. 587-590.

Galioto, et al., *Right coronary artery to left ventricle fistula*, AHJ, vol. 82, No. 1, (Jul. 1971), No. 1, p. 93-97.

Levinsky, et al., *The Revival of the Horseshoe Graft*, The Thoracic and Cardiovascular Surgeon, vol. 27, No. 5, (Oct. 1979), pp. 281-344.

Medical Industry Today Headline News, Device and Diagnostics, (Jul. 17, 1998), Article # 07179802, Article is 349 words long, pp. 1-2.

Medical Industry Today Headline News, Financial News, (Jul. 17, 1998), Article 07179808, article is 560 words long, pp. 1-2.

Munro, et al., *The possibility of myocardial revascularization by creation of a left ventriculocoronary artery fistula*, The Journal of Thoracic and Cardiovascular Surgery, vol. 58, (1969), pp. 25-32.

Bohning, et al., *The Thebesian Vessels as a Source of Nourishment for the Myocardium*, From the Cardiovascular Laboratory, Department of Physiology, Michael Reese Hospital, Chicago, Received for publication on Jun. 23, 1933.

Oesterle, et al., *Catheter-Based Coronary Bypass: A Development Update*, Catheterization and Cardiovascular Interventions, vol. 58, (2003), pp. 212-218.

Goldman, et al. *Experimental Methods for Producing a Collateral Circulation to the Heart Directly from the Left Ventricle*, J. Thoracic Surgery, vol. 31, No. 3 (Mar. 1956) pp. 364-374.

Cohen et al., *Alternative Approach to Coronary Revascularization*, Current International Cardiology Reports, vol. 1 (1999), pp. 138-146.

US 6,331,185, 12/2001, Gambale et al. (withdrawn)

* cited by examiner

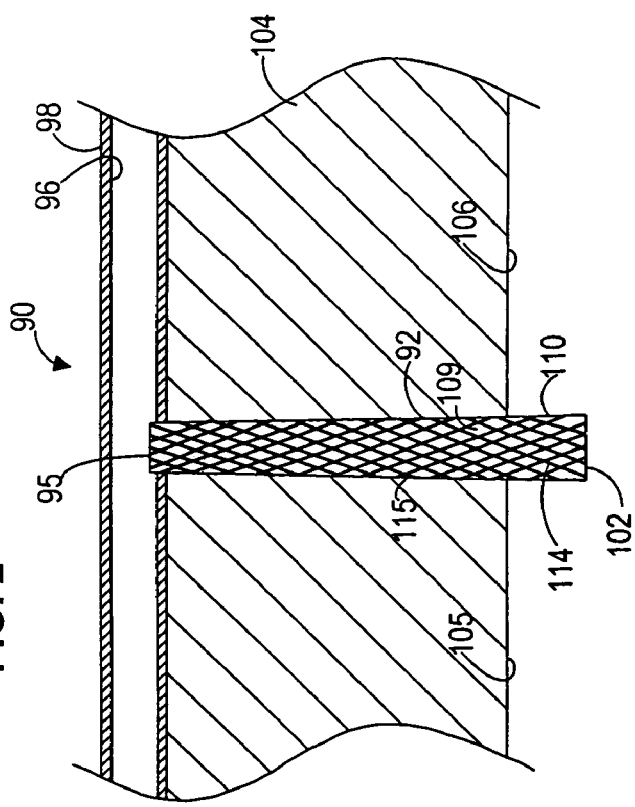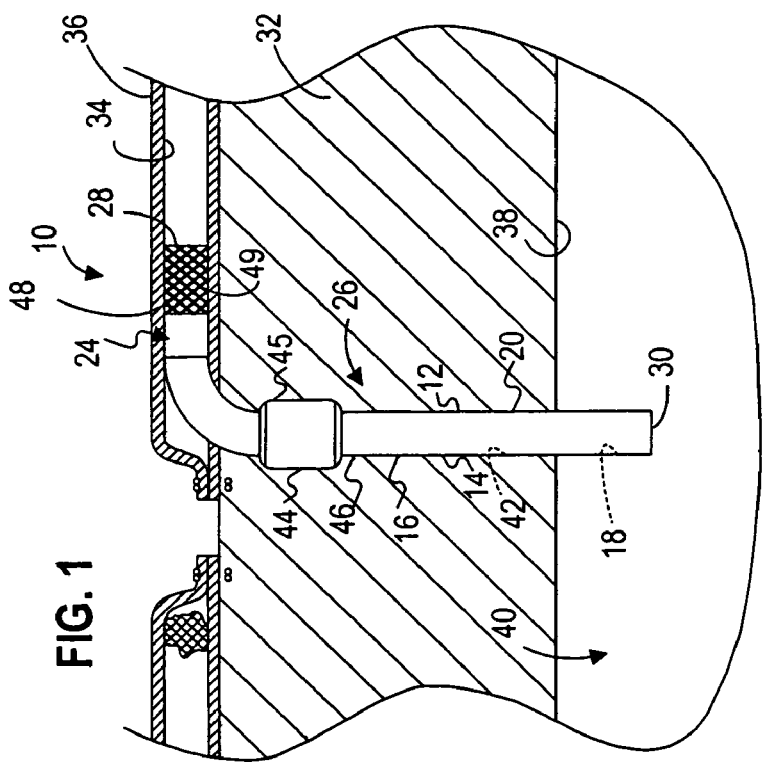

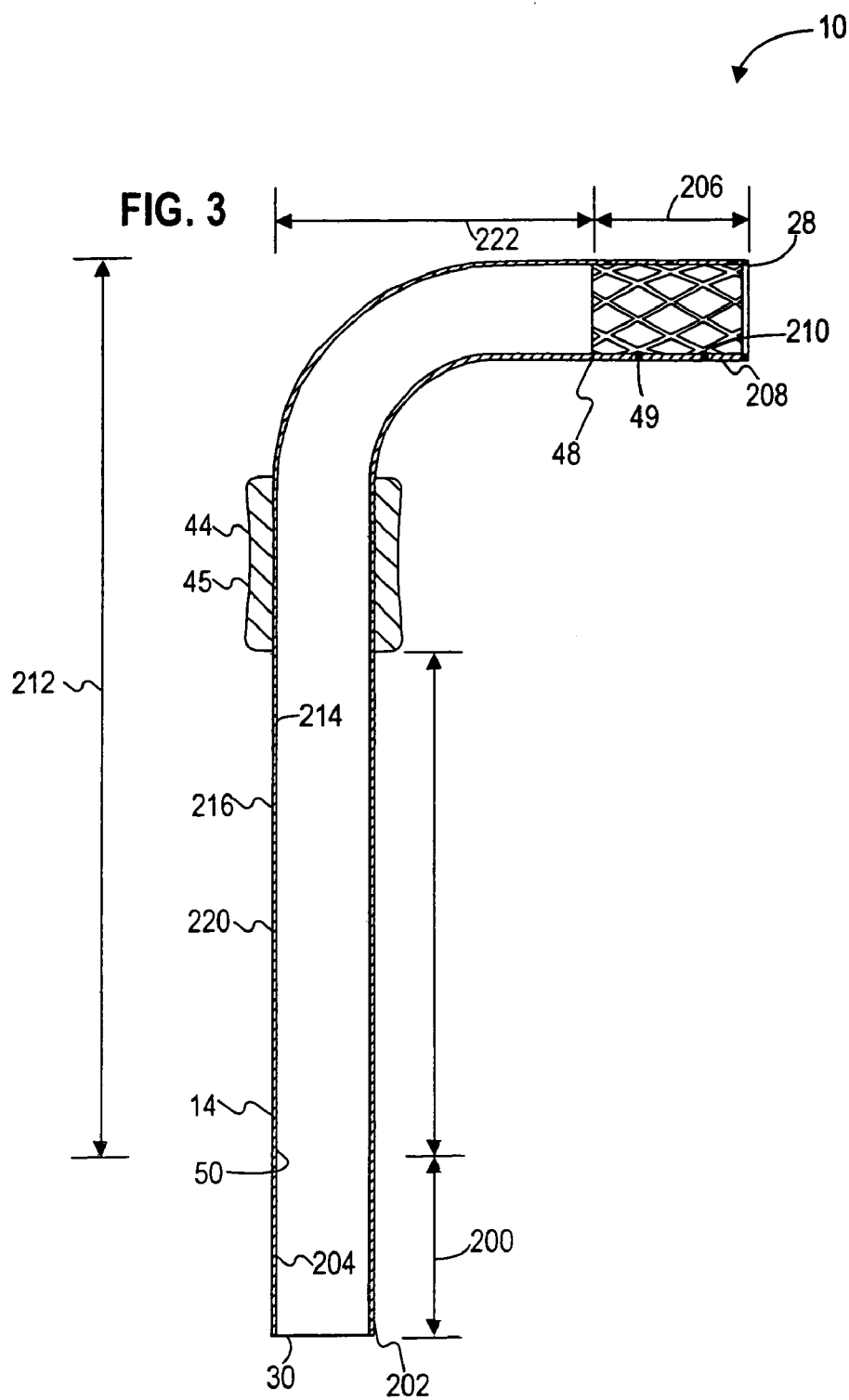

CARDIAC IMPLANT AND METHODS

TECHNICAL FIELD

This disclosure relates to cardiac implants, methods of making, and methods of using.

BACKGROUND

U.S. Pat. No. 5,944,019, issued Aug. 31, 1999, teaches an implant for defining a blood flow conduit directly from a chamber of the heart to a lumen of a coronary vessel. An embodiment disclosed in this patent teaches an L-shaped implant in the form of a rigid conduit having one leg sized to be received within a lumen of a coronary artery and a second leg sized to pass through the myocardium and extend into the left ventricle of the heart. As disclosed in the '019 patent, the conduit is rigid and remains open for blood flow to pass through the conduit during both systole and diastole. The conduit penetrates into the left ventricle in order to prevent tissue growth and occlusions over an opening of the conduit. U.S. Pat. No. 5,944,019 is incorporated by reference herein.

U.S. Pat. No. 5,984,956, issued Nov. 16, 1999, discloses an implant with an enhanced fixation structure. The enhanced fixation structure includes a fabric surrounding at least a portion of the conduit to facilitate tissue growth on the exterior of the implant. U.S. Pat. No. 5,984,956 is incorporated herein by reference. U.S. Pat. No. 6,029,672 issued Feb. 29, 2000 teaches procedures and tools for placing a conduit. U.S. Pat. No. 6,029,672 is incorporated herein by reference.

Improvements in implants continue to be desirable.

SUMMARY OF THE DISCLOSURE

Cardiac implants are disclosed including a conduit or scaffold having a first therapeutic agent in at least partial covering relation to at least a first portion of the scaffold, and a second therapeutic agent, different from the first therapeutic agent, in at least partial covering relation to at least a second portion of the scaffold.

In some embodiments, the first therapeutic agent may include one of: antithrombotic agents, anti-inflammatory agents, antiproliferative agents, antibiotic agents, angiogenic agents, antiplatelet agents, anticoagulant agents, rhestenosis preventing agents, hormones and combinations thereof. The second therapeutic agent will preferably be different from the first therapeutic agent and can include any of the following types of therapeutic agents: antithrombotic agents, anti-inflammatory agents, antiproliferative agents, antibiotic agents, angiogenic agents, antiplatelet agents, anticoagulant agents, rhestenosis preventing agents, hormones and combinations thereof.

Methods for making cardiac implants are described herein. Preferred methods include providing a scaffold, covering at least a first portion of the scaffold with a first therapeutic agent, and covering at least a second portion of the scaffold, different from the first portion, with a second therapeutic agent different from the first therapeutic agent.

Methods for treating a patient and for using cardiac implants are provided herein. One method is described as performing a coronary vessel bypass procedure. The method includes forming a blood flow path from a heart chamber directly to the coronary vessel, which includes placing a conduit in a heart wall between the chamber and the vessel with the first end of the conduit protruding into the chamber and protruding beyond an interior surface of the heart wall. The conduit will include a first therapeutic agent in covering relation to at least a first portion of the conduit and a second therapeutic agent in covering relation to at least a second portion.

BRIEF DESCRIPTION OF THE DRAWINGS

FIG. 1 is a side sectional view of one embodiment of an implant shown in place in a human heart wall with the implant establishing a direct blood flow path from a heart chamber to a coronary vessel, constructed according to principles of this disclosure;

FIG. 2 is a side sectional view of a second embodiment of an implant shown in place in a human heart wall, constructed according to principles of this disclosure;

FIG. 3 is an enlarged, cross-sectional view of the implant shown in FIG. 1 and depicting zones for the application of therapeutic agents;

DETAILED DESCRIPTION

Figure 4:
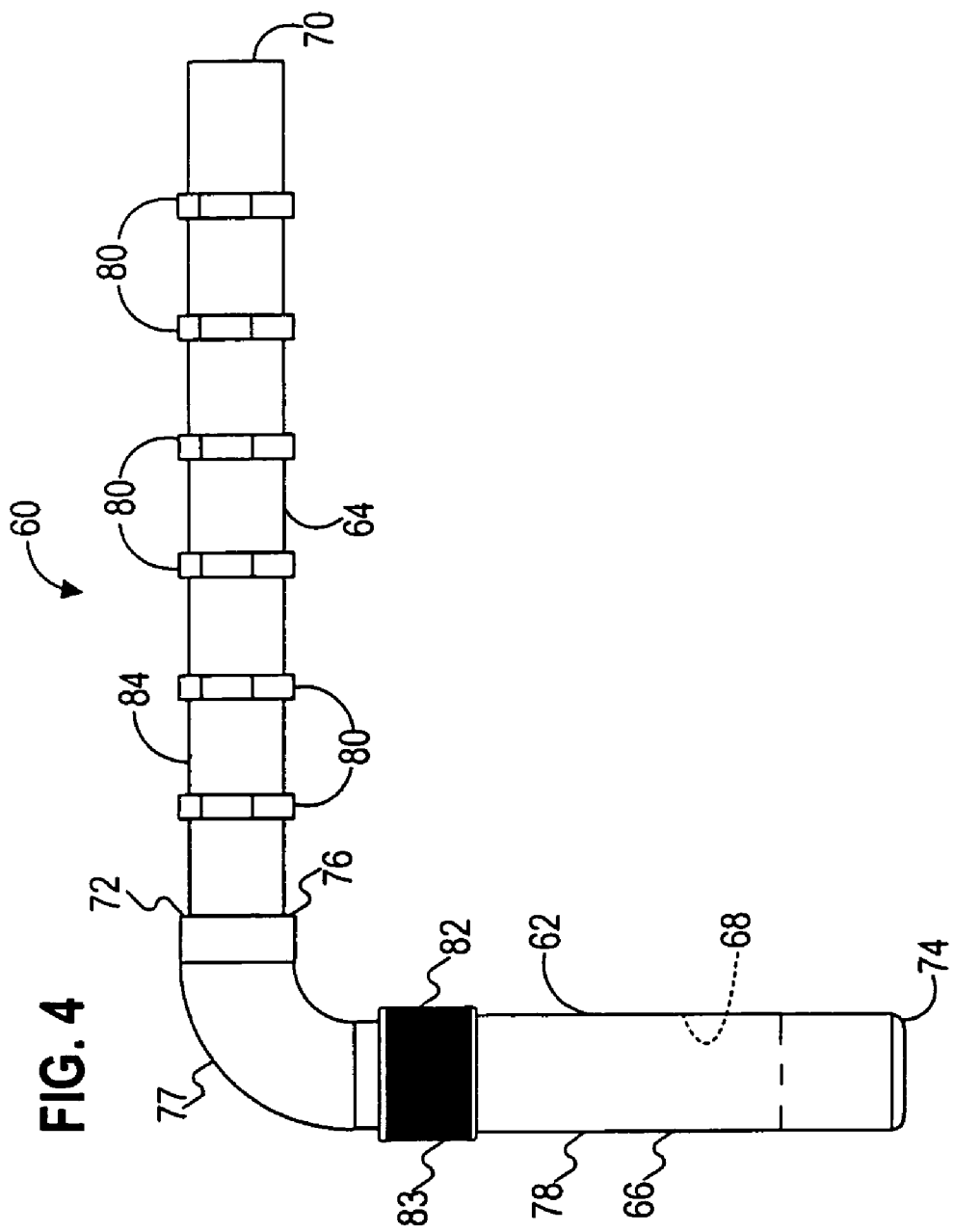
FIG. 4 is a side elevational view of another embodiment of an implant of the type shown in FIG. 1.

A. Potential Adverse Events Following Placement of Intracardiac/Intracoronary Devices (i) Restenosis Restenosis is the closure of a coronary artery following trauma to the artery caused by, for example, efforts to open a stenosed portion of the artery. Restenosis is believed to arise through the proliferation and migration of cellular components from the arterial wall, as well as through geometric changes in the arterial wall referred to as "remodelling".

Restenosis following angioplasty treatment remains a significant problem that is believed to be caused by efforts to open an occluded portion of the artery by angioplasty, such as, for example, by balloon dilation, atherectomy or laser ablation treatment of the artery. For these angioplasty procedures, restenosis occurs at a rate of about 30–60% depending upon the vessel location, lesion length and a number of other variables. Restenosis typically occurs within the first six months after angioplasty.

One aspect of restenosis may be simply mechanical; e.g. caused by the elastic rebound of the arterial wall and/or by dissections in the vessel wall caused by the angioplasty procedure. These mechanical problems have been successfully addressed by the use of stents to tack-up dissections and prevent elastic rebound of the vessel, thereby reducing the level of restenosis for many patients. The stent is typically inserted by catheter into a vascular lumen and expanded into contact with the diseased portion of the arterial wall, thereby providing internal support for the lumen. Examples of stents that have been successfully applied over a PTCA balloon and radially expanded at the same time as the balloon expansion of an affected artery include the stents disclosed in: U.S. Pat. No. 4,733,665 issued to Palmaz; U.S. Pat. No. 4,800,882 issued to Gianturco; and U.S. Pat. No. 4,886,062 issued to Wiktor, each of which is incorporated herein by reference in its entirety.

Another aspect of restenosis is believed to be a natural healing reaction to the injury of the arterial wall that is caused by angioplasty procedures. The healing reaction begins with the thrombotic mechanism at the site of the injury. The final result of the complex steps of the healing process is intimal hyperplasia, the migration and proliferation of medial smooth muscle cells, until the artery is again occluded.

In an attempt to prevent restenosis, metallic intravascular stents have been permanently implanted in coronary or peripheral vessels. The stent is typically inserted by catheter into a vascular lumen and expanded into contact with the diseased portion of the arterial wall, thereby providing mechanical support for the lumen. However, it has been found that restenosis can still occur with such stents in place. Also, the stent itself can cause undesirable local thrombosis. To address the problem of thrombosis, persons receiving stents also receive extensive systemic treatment with anticoagulant and antiplatelet drugs.

To address the restenosis problem, it has been proposed to provide stents that are seeded with endothelial cells (Dichek, D. A. et al Seeding of Intravascular Stents With Genetically Engineered Endothelial Cells; Circulation 1989; 80: 1347–1353). In that experiment, sheep endothelial cells that had undergone retrovirus-mediated gene transfer for either bacterial beta-galactosidase or human tissue-type plasminogen activator were seeded onto stainless steel stents and grown until the stents were covered. The cells were therefore able to be delivered to the vascular wall where they could provide therapeutic proteins. Other methods of providing therapeutic substances to the vascular wall by means of stents have also been proposed such as in international patent application WO 91/12779 "Intraluminal Drug Eluting Prosthesis" and international patent application WO 90/13332 "Stent With Sustained Drug Delivery". In those applications, it is suggested that antiplatelet agents, anticoagulant agents, antimicrobial agents, anti-inflammatory agents, antimetabolic agents and other drugs could be supplied in stents to reduce the incidence of restenosis. Further, other vasoreactive agents such as nitric oxide releasing agents could also be used.

(ii) Vascular Damage

Implanting a stent may lead to dissection of the vessel distal and/or proximal to the stented portion and may cause acute closure of the vessel requiring additional intervention (e.g. CABG, further dilation, placement of additional stents, or other).

(iii) Blood Clotting Disorders

Placement of the device carries an associated risk of subacute thrombosis, vascular complications, and/or bleeding events.

(iv) Delayed Disorders

Placement of intracardiac/intracoronary devices may lead to delayed disorders such as: aneurysm, arrhythmias, bleeding complications, distal emboli, emergent CABG, myocardial infarction, myocardial ischemia, occlusion, stent delivery failures, target lesion revascularization, thrombosis, vascular complications, vessel dissection.

B. Example Environments of Use

With initial reference to FIGS. 1 and 3, an implant is shown generally at 10. The implant 10 includes a composite of a hollow, rigid scaffold or conduit 12. The conduit 12 includes a wall 14 defining an outer surface 16 and a hollow interior 18. In preferred embodiments, the wall 14 has a circular cross-section, forming a tube or cylinder 20. The conduit 12 includes a second portion 24, preferably corresponding to a vessel or vasculature portion, and a first portion 26, generally corresponding to a myocardial portion. The conduit 12 includes an open second end 28 that is defined by the vascular portion 24. The conduit 12 also includes an open first end 30 that is defined by the myocardial portion 26. The open second end 28 may be anastomosed to a vessel with sutures (not shown) in an end-to side anastomosis as is done in conventional coronary artery bypass procedures.

In FIG. 1, a cross-section of the myocardium 32 of a human heart is shown. As can be seen in FIG. 1, in preferred embodiments, the second portion 24 is dimensioned to be received within a lumen 34 of a coronary vasculature 36. As used herein, the term "vasculature" refers to veins or arteries. Note that the vasculature 36 resides exterior of the myocardium 32. The first portion 26 is dimensioned to extend from the vasculature 36 through the myocardium 32 and into a heart chamber 38. In preferred implementations, the heart chamber 38 will be the left ventricle 40. As can be seen in FIG. 1, the conduit 12 defines a blood flow pathway 42 within the interior 18 between the open first end 30 and the open second end 28. This allows for the flow of oxygenated blood directly from the left ventricle 40 through the pathway 42 and into the vasculature 36. The distal end 48 of the vascular portion 24 is shown connected to an intravascular stent 49. In the embodiment shown, the end 30 corresponds to an inlet end 30 and the end 28 corresponds to an outlet end 28.

As discussed more fully in U.S. Pat. No. 5,984,956, the conduit 12 may be provided with tissue-growth producing material 44 adjacent the upper end 46 of the first portion 26 to immobilize the conduit 12 within the myocardium 32. The material 44 surrounds the exterior of the conduit 12 and may be a polyester woven cuff 45 or sintered metal to define pores into which tissue growth from the myocardium 32 may occur.

In the preferred embodiment, the implant 10 will have an outside diameter $D_O$ of about 1 to 3 millimeters and an internal diameter $D_I$ of about 0.5 to 2.5 millimeters to provide a wall thickness of about 0.5 millimeters. By way of non-limiting example, a specific $D_O$ may be 2.5 millimeters and a specific $D_I$ may be 2.0 millimeters.

The size range given permits insertion of the conduit into a coronary vessel to be bypassed. Commonly, such vessels in an adult human have internal diameters of 1 to 3 millimeters when under the influence of normal pressurized blood flow.

With reference to FIG. 4, a further embodiment of an implant 60 is shown. This embodiment can be used in a similar manner to the embodiment illustrated in FIG. 1. The embodiment shown in FIG. 4 includes a composite of a hollow, rigid cylindrical scaffold or conduit 62 and a flexible conduit 64. The conduit 62 may be formed of suitable material such as low density polyethylene ("LDPE"). The material of the conduit 62 is preferably a rigid material in order to withstand contraction forces of the myocardium and hold open a path through the myocardium during both systole and diastole.

The implant 60 includes a sleeve 66 of tissue growth-inducing material secured to an exterior surface of the conduit 62. In the embodiment of FIG. 4, the sleeve 66 resides exclusively on the rigid cylindrical conduit 62 in order to reside exclusively within the myocardium 32 after surgical placement of the implant. (See generally, FIG. 1) Preferably, the sleeve 66 is formed of a fabric having biocompatible fibers defining interstitial spaces to receive tissue growth. An example of such a fabric is polyethylene terephthalate (such as polyester fabric sold by DuPont Company under the trademark Dacron). Such a fabric permits rapid tissue integration into the fabric to anchor the fabric and, hence, the conduit 62 to the patient's tissue. As a result the sleeve 66 is selected to induce tissue attachment. As can be appreciated from a review of the cross-section shown in FIG. 5, the sleeve 66 wraps around and engages against the inner surface and outer surface of the rigid conduit 62. In the embodiment shown, the sleeve 66 extends from the end 74 to a region adjacent to the elbow 77 of the implant 60.

It will be appreciated the description of a sleeve as described is the subject of commonly assigned and copending U.S. patent application Ser. No. 08/944,313 filed Oct. 6, 1997 entitled "Transmyocardial Implant", and filed in the name of inventors Katherine S. Tweden, Guy P. Vanney and Thomas L. Odland. The disclosure of Ser. No. 08/944,313 is incorporated by reference herein.

In this embodiment, the conduit 62 is sized to extend through the myocardium 32 of the human heart to project into the interior of a heart chamber (preferably, the left ventricle 40) by a distance of about 5 mm. (See generally, FIG. 1) The conduit 62 extends from a second (or upper) end 72 to a first (or lower) end 74. The flexible conduit 64 has first and second ends 76, 78 (FIG. 4). A first end 76 of the flexible conduit 64 is secured to the rigid conduit 62 by heat bonding along all surfaces of opposing material of the rigid conduit 62 and the flexible conduit 64. At elevated temperatures, the material of the rigid conduit 62 flows into the micro-pores of the material of the flexible conduit 64. The rigid material has a lower melting point than the flexible material.

The rigid conduit 62 and attached flexible conduit 64 are placed in the myocardium 32, 232 with the lower end 74 protruding into the left ventricle 40. (See generally, FIG. 1) The implant 60 thus defines an open blood flow path 68 having end 74 in blood flow communication with the left ventricle. A second end 70 of the blood flow path 68 communicates directly with the lumen of the coronary vessel lying at an exterior of the heart wall. (See generally, FIG. 1) To bypass an obstruction in a coronary artery, the vascular end 78 of the flexible conduit 64 may be attached to, or lie within, the artery in any suitable manner.

In the particular embodiment illustrated, a plurality of discrete rigid rings 80 are provided along the length of the flexible conduit 64. Preferably, the rings 80 are LDPE each having an interior surface heat bonded to an exterior surface of the flexible conduit 64. The rings 80 provide crush resistance. Between the rings 80, the flexible conduit 64 may flex inwardly and outwardly to better simulate the natural compliance of a natural blood vessel. By way of a further non-limiting example, the discrete rings 80 could be replaced with a continuous helix.

As discussed more fully in U.S. Pat. No. 5,984,956, the rigid conduit 62 may be provided with tissue-growth producing material 82 adjacent the upper end of the conduit 62 to immobilize the conduit 62 within the myocardium 32. The material 82 surrounds the exterior of the conduit 62 and may be a polyester woven cuff 83 or sintered metal to define pores into which tissue growth from the myocardium may occur.

A further embodiment of the invention is described with reference to FIGS. 2, and 6. In FIG. 2 an implant 90 is shown including a straight elongate, generally cylindrical tube, scaffold, or conduit 92. The conduit 92 may be formed of titanium or other rigid biocompatible material such as pyrolytic carbon or may be titanium coated with pyrolytic carbon. Preferably, an interior wall 94 of the conduit 92 is polished to a high degree of polish to reduce the likelihood of thrombus formation on the wall. The material of the conduit 92 is preferably a rigid material in order to withstand contraction forces of the heart wall, as will be described. As can be seen in FIG. 2, preferably, the conduit 92 is straight and bend-free.

The tube 92 has a second open end 95 which is sized to be received within the lumen of a coronary vessel such as the lumen 96 of a coronary artery 98. The illustrated embodiment depicts bypassing a coronary artery with blood from a left ventricle. The invention is equally applicable to forming a blood flow path within the vessels; or from other heart chambers to other coronary vessels.

The conduit 92 has a first open end 102. The conduit 92 is sized to extend from the coronary artery 98 directly through the heart wall 104 and protrude into the left ventricle 106 of a human heart. Preferably, the end 102 protrudes at least about 5 millimeters from an inner surface 105 of the heart wall 104 during maximum heart wall thickness during systole. Heart wall thickness varies from human to human and among locations on the heart. In a preferred embodiment of forming a flow path from the left ventricle to a coronary artery of an adult human, the length of the conduit (measured as the axial distance between ends 95 and 102) will be between about 10 and 30 millimeters. With the foregoing specific example, for a heart wall 104 having a maximum systolic thickness of 20 millimeters, the length of the conduit 92 is 25 millimeters.

The openings 95, 102 communicate with an interior volume 108 of the conduit 92. Therefore, blood can freely flow through the conduit 92 between the left ventricle 106 and the lumen 96 of the coronary artery 98.

As mentioned, the tube 92 is preferably formed of titanium or other smooth biocompatible material in order to resist thrombus formation on the inner surface 94 of the conduit 92. Titanium is a presently preferred material due its long-term use in the cardiovascular industry. Further, titanium is sufficiently rigid to withstand deformation forces caused by contraction of the heart wall 104 to avoid deformation of the tube 92 so that the tube 92 remains open during both diastole and systole. Also, the tube 92 is solid on its inner surface 94. Therefore, highly thrombogenic material from the heart wall 104 cannot pass into and contaminate the interior 108 of the conduit 92.

In one embodiment, the tube 92 may preferrably be formed from titanium which is resistant to thrombus formation. Therefore, as the titanium of the cylindrical tube 92 does not attach the device within the myocardium or heart wall 104, the implant 90 may include a sleeve 110 of tissue growth-inducing material. This sleeve 110 is secured to an exterior surface 112 of the conduit 92. In the embodiment shown, the sleeve 110 is formed as a grid or matrix 114 of expanded metal or other materials to provide a porous but uniform covering 115 from end 95 to end 102.

The conduit 92 is sized to extend from the coronary artery directly through the heart wall 104 and protrude into the left ventricle 106 of the patient's heart. Preferably, the end 102 protrudes at least about 5 millimeters from the inner surface 105 of the heart wall during maximum heart wall thickness during systole. The openings 95, 102 communicate with interior 108 of the conduit 92. Therefore blood can freely flow through the conduit 92 between the left ventricle 106 and the lumen 96 of the coronary artery 98.

C. The Use of "Drugs" or "Therapeutic Agents" with Cardiac Implants

1. Anticoagulant Agents

In patients with arterial thrombi, activation of platelets is considered central to the thrombotic complications of these disorders. Treatment with platelet-inhibiting drugs such as aspirin and ticlopidine or clopidogrel is indicated in patients with unstable angina and acute myocardial infarction. In angina and infarction, these drugs are often used in conjunction with fibrinolytic drugs and anti-glycoprotein IIb/IIIa platelet inhibitors.

When a blood vessel is damaged or subject to disruption the immediate hemostatic response is vasospasm. Within seconds, platelets stick to the exposed collagen of the damaged endothelium (platelet adhesion) and to each other (platelet aggregation). Platelets then form a clumped gelatinous mass (viscous metamorphosis). This platelet plug quickly arrests bleeding but must be reinforced by fibrin for long-term effectiveness. Blood coagulates by the transformation of soluble fibrinogen into insoluble fibrin due to the action of several circulating proteins that interact in a cascading series of limited reactions.

Blood coagulation generally requires the participation of several plasma protein coagulation factors: factors XII, XI, IX, X, VIII, VII, V, XIII, prothrombin, and fibrinogen, in addition to tissue factor (factor III), kallikrein, high molecular weight kininogen, Ca.sup.+2, and phospholipid. The final event is the formation of an insoluble, cross-linked polymer, fibrin, generated by the action of thrombin on fibrinogen. Fibrinogen has three pairs of polypeptide chains (ALPHA 2-BETA 2-GAMMA 2) covalently linked by disulfide bonds with a total molecular weight of about 340,000. Fibrinogen is converted to fibrin through proteolysis by thrombin. An activation peptide, fibrinopeptide A (human) is cleaved from the amino-terminus of each ALPHA chain; fibrinopeptide B (human) from the amino-terminus of each BETA chain. The resulting monomer spontaneously polymerizes to a fibrin gel. Further stabilization of the fibrin polymer to an insoluble, mechanically strong form, requires cross-linking by factor XIII. Factor XIII is converted to XIIIa by thrombin in the presence of Ca.sup.+2. XIIIa cross-links the GAMMA chains of fibrin by transglutaminase activity, forming EPSILON-(GAMMA-glutamyl) lysine cross-links. The ALPHA chains of fibrin also may be secondarily cross-linked by transamidation.

Anticoagulant agents interrupt and/or inhibit coagulation cascade and subsequent thrombosis.

Example: Heparin. Heparin inhibits reactions that lead to the clotting of blood and the formation of fibrin clots. Heparin acts at multiple sites in the normal coagulation system. Small amounts of heparin in combination with antithrombin III (heparin cofactor) can inhibit thrombosis by inactivating activated Factor X and inhibiting the conversion of prothrombin to thrombin. Once active thrombosis has developed, larger amounts of heparin can inhibit further coagulation by inactivating thrombin and preventing the conversion of fibrinogen to fibrin. Heparin also prevents the formation of a stable fibrin clot by inhibiting the activation of the fibrin-stabilizing factor. Low MW heparin may also be used.

Other Examples: Hirudin; mitric acid; hirulog; and annexim II.

2. Antiplatelet Agents

Platelet function is regulated by three categories of substances. The first group consists of agents generated outside the platelet that interact with platelet membrane receptors e.g. catecholamines, thrombin, and prostacyclin. The second category contains agents generated within the platelet that interact with the membrane receptors. The third group contains those agents generated within the platelet that act within the platelet such as thromboxane $A_2$.

Antiplatelet agents prevent adhesion, activation, and/or aggregation; prevent thrombosis; prevent smooth muscle cell activation; and prevent growth factor release (by inhibiting platelets) and all the subsequent sequeale (tissue proliferation).

Example: Aspirin. Thromboxane $A_2$ causes platelets to change shape, to release their granules and to aggregate. Aspirin is the prototype of the class of drugs that inhibit the generation of thromboxane $A_2$, a powerful inducer of platelet aggregation and vasoconstriction. Aspirin is a potent inhibitor of prostaglandin synthesis.

Other Examples: iclopidine; clopidogrel; dipyridamole; gpIIbIIIa antibodies; and nitric oxide.

3. Antithrombotic Agents or Fibrinolytics

Antithrombotic agents are used to dissolve blood clots that have formed in certain blood vessels when a blood clot seriously lessens the flow of blood to certain parts of the body. Antithrombotic agents are also used to dissolve blood clots that form in tubes that are placed into the body. Antithrombotic drugs rapidly lyse thrombi by catalyzing the formation of the serine protease plasmin from its precursor zymogen, plasminogen. By creating a generalized lytic state, thrombo-emboli are broken down.

Example: Streptokinase. Streptokinase is a protein that combines with the proactivator plasminogen. The resulting enzymatic complex catalyzes the conversion of inactive plasminogen to active plasmin.

Other Examples: Tpa (raw or delivered via genetically engineered cells); and urokinase.

4. Antimicrobials/Antibiotics

The activity of antimicrobial drugs is due to their selectivity for highly specific targets that are either unique to microorganisms or much more important in them than in humans. Among those targets are specific bacterial and fungal cell wall-synthesizing enzymes, the bacterial ribosome, the enzymes required for nucleotide synthesis and DNA replication, and the machinery of viral replication.

Antibiotics prevent infection; may prevent/inhibit cell proliferation; and may prevent/inhibit thrombus accumulation.

Examples include: silver; silver combined with more noble metals (Pb, Pt, Au) to enhance ionization; silver oxide; heavy metals; vancomycin; rifampin; and other common antibiotics.

5. Antiproliferatives

Antiproliferative agents prevent proliferation of the offending cell types, e.g. smooth muscle cells or fibroblasts.

An example of an antiproliferative agent includes a microtubule stabilizing agent such as paclitaxel (taxol), analogues, derivatives, and mixtures thereof. For example, derivatives believed suitable for use in the present invention include 2'-succinyl-taxol, 2'-succinyl-taxol triethanolamine, 2'-glutaryl-taxol, 2'-glutaryl-taxol triethanolamine salt, 2'-O-ester with N-(dimethylaminoethyl) glutamine, and 2'-O-ester with N-(dimethylaminoethyl) glutamide hydrochloride salt.

Other examples include: Sirolimus; napamycin; actinomycinD; antigrowth factor antibodies (e.g. antiPDGF antibody); radiation therapy ($\lambda$ or $\beta$); and nitric oxide.

6. Anti-Inflammatories

Inflammatory by-products have been shown to play a role in tissue proliferation. These agents have been shown to inhibit proliferation.

Example: nonsteroidal anti-inflammatory drugs (NSAIDS). Salicylates and other similar agents have the capacity to suppress the signs and symptoms of inflammation. The NSAIDS are grouped in several chemical classes. This chemical diversity yields a broad range of pharmacokinetic characteristics. The anti-inflammatory activity of the NSAIDS is mediated chiefly through inhibition of biosynthesis of prostaglandins. To varying degrees all the newer NSAIDS are anti-inflammatory and inhibit platelet aggregation.

Example: Steroids. The glucocorticoids have powerful anti-inflammatory effects. Long term use of corticosteriod therapy produces significant toxicity.

7. Growth Factors

Growth factors stimulate chemotaxis and proliferation of appropriate cell types to promote healing (e.g., endothelium) and angiogenesis.

Examples of growth factors include: FGF family (a or bFGF, FGF 1-4); PDGF; VEGF; EFG; and IGFI II. Growth factors can be directly attached, delivered from a microsphere, polymer, etc.

8. Cell Adhesion Molecules/Peptides

Cell adhesion molecules/peptides promote cell attachment for decreased thrombus formation and promotion of tissue incorporation.

Examples include: RDG peptides; REDV peptides; laminin or fragments thereof; collagen or fragments thereof; fibronectin/fibrin or fragments thereof; and integrins.

9. Passivating Coatings

Passivating coatings reduce thrombus accumulation and biofouling. Passivating coatings also reduce foreign body response, such as inflamation and fibrosis. Such coatings can also reduce tissue proliferation.

Examples of passivating coatings include: Hydrogels, phospholipids in general, and specifically phosphotidyl choline; gold; silicon carbide; and polyethylene oxides or polyethylene glycol.

10. Cell Seeding

Cell seeding lines conduits with endothelium to promote healing and subsequent passivasion. Endothelium could be genetically modified to secrete antiplatelets and/or anticoagulants to inhibit thrombosis.

11. Hormones

Some hormones have been shown useful to inhibit intimal hyperplasia.

An example of one useable hormones is estrogen.

D. Example Applications of Therapeutic Agents with Cardiac Implants

1. Cardiac Implant Zones

The embodiments of the invention described above have an inflow end 30, 74, 102 and an outflow end 28, 70, 95. As can be recognized, the inflow end 30, 74, 102 is situated in a cardiac chamber and the outflow end 28, 70, 95 is situated in a coronary vessel. (See, for example, FIG. 1)

In the embodiment shown, each of the inflow ends 30, 74, 102 has, adjacent to it, an "inlet zone" 200. Each inlet zone 200 has an exterior inlet zone 202, located on the exterior wall of the implant 10, 60, 90 as well as an interior inlet zone located on an interior surface of the wall of each implant 10, 60, 90. As will be explained further below, preferred embodiments will include the application of therapeutic agents on the inlet zone 200. In general, for the embodiments of the type shown herein, the inlet zone 200 will extend from the inlet end 30, 74, 102 along the implant 10, 60, 90 for a distance no greater than 0.5 inches. In some applications, the inlet zone 200 will be only the tip of the implant 10, 60, 90, and thus extend from the end 30, 74, 102 to a distance of 3 mm or less.

Analogously, each of the outflow ends 28, 70, 95 includes adjacent to it an "outlet zone" 206. Each outlet zone 206 includes an exterior outlet zone 208 and an interior outlet zone 210, located on the exterior surface and interior surface, respectively, of each implant 10, 60, 90. Preferred embodiments will include application of selected therapeutic agents along the outlet zone 206. For the types of implants described herein, preferably, the outlet zone 206 extends from the outlet end 28, 70, 95 a distance no greater than 3.75 inches. Again, the outlet zone 206 may also just extend only at the tip of the outlet end, and thus extend from the end 28, 70, 95 a distance of 3 mm or less.

Located in between the inlet zone 200 and the outlet zone 206 is at least one mid zone 212. In some embodiments, the mid zone 212 may include a plurality of mid zones 212 located between the inlet zone 200 and the outlet zone 206. The mid zone 212 includes a mid interior zone 214, which is located along the interior wall of each implant 10, 60, 90, and a mid exterior zone 216 located on the exterior wall of each implant 10, 60, 90. As with the inlet zone 200 and the outlet zone 206, the mid zone 212 includes, in preferred embodiments, selected therapeutic agents applied thereon. This is discussed further below.

2. The Use of Therapeutic Agents in Various Zones

The introduction of a foreign body such as the cardiac implants 10, 60, 90 into the heart or a blood vessel provides a surface on which blood coagulation may occur. The end result of the process of blood coagulation is the formation of fibrin blood clots. The term "fibrin" means the naturally occurring polymer of fibrinogen that arises during blood coagulation. One effect that the formation of fibrin blood clots may have is to obstruct the inflow end 30, 74, 102 and/or the outflow end 28, 70, 95 of the implant 900. Furthermore, there is the danger that pieces of tissue may break off from the developed fibrin blood clots. These pieces of fibrin blood clot (called "emboli") can travel in the blood stream and obstruct other vessels thereby producing obstruction of blood flow in those vessels. For example, an embolus in a cerebral vessel that produces obstruction may result in neurological damage in a process described as a "stroke". Use of a drug, such as an anticoagulant agent, an antithrombolic agent, or a fibrimolytic agent to inhibit thrombosis, the formation of fibrin blood clots, at the inlet zone 200 and the outlet zone 206 may be protective in this regard.

The inlet zone 200 may also be prone to tissue proliferation. Thus, use of a therapeutic agent, such as an anti-inflammatory and/or an anti-proliferative agent may be useful. In addition, anti-platelet agents applied to the inlet zone 200 can be useful to prevent adhesion, activation, aggregation and prevent thrombosis, smooth muscle cell activation, growth factor release, and subsequent tissue proliferation.

In addition to the anti-coagulant agents, anti-thrombotic agents, and fibronylet(spelling) agents applied to the outlet zone 206, in many instances, it may be useful to apply anti-proliferative agents, antibiotics, anti-platelets and hormones to the outlet zone 206.

The mid zone 212 can be subject to thrombosis, cell proliferation, and/or infection. In many applications, it can be useful to apply therapeutic agents such as anit-thrombotic, antibiotics, and anti-inflammatories.

3. Example Applications of Therapeutic to the Illustrated Embodiments

First, attention is directed to the first embodiment of the implant 10 shown in FIGS. 1 and 3. In this particular embodiment, the mid zone 212 includes at least two subzones. In particular, there is a first mid subzone 220, corresponding to the myocardium portion 26 of the implant 10, and a second sub mid zone 222 corresponding to the vessel portion 24. Of course, in other embodiments, the mid zone 212 can include additional subzones, depending upon the desired results and the particular conditions of the patient. In Table 1, below, specific examples are provided for the implant 10 illustrated in FIGS. 1 and 3.

Implant 10 has the interface 48 between the stent 49 and the conduit 12. At this interface 48, it may be advantageous to change coatings and/or dosages of the therapeutic agent. The interface 48 is a region that may be prone to the formation of stenosis. To control the formation of stenosis, changing the type of therapeutic agent that is located on the stent 49 than what is located on the conduit 12 may be desirable. Alternatively, instead of changing the type of therapeutic agent on the conduit 12 from the type on the stent 49, the therapeutic agent may be kept the same but the amount or dosage may be differentiated between these two areas.

In many cases, the inner surface of the entire implant 10 will be made of a highly polished material. Highly polished materials may not have surfaces conducive for the deposition of drugs or therapeutic agents. However, the implants 10 can be manufactured such that the inner surface allows for a surface treatment with a desired therapeutic agent.

Figure 5:
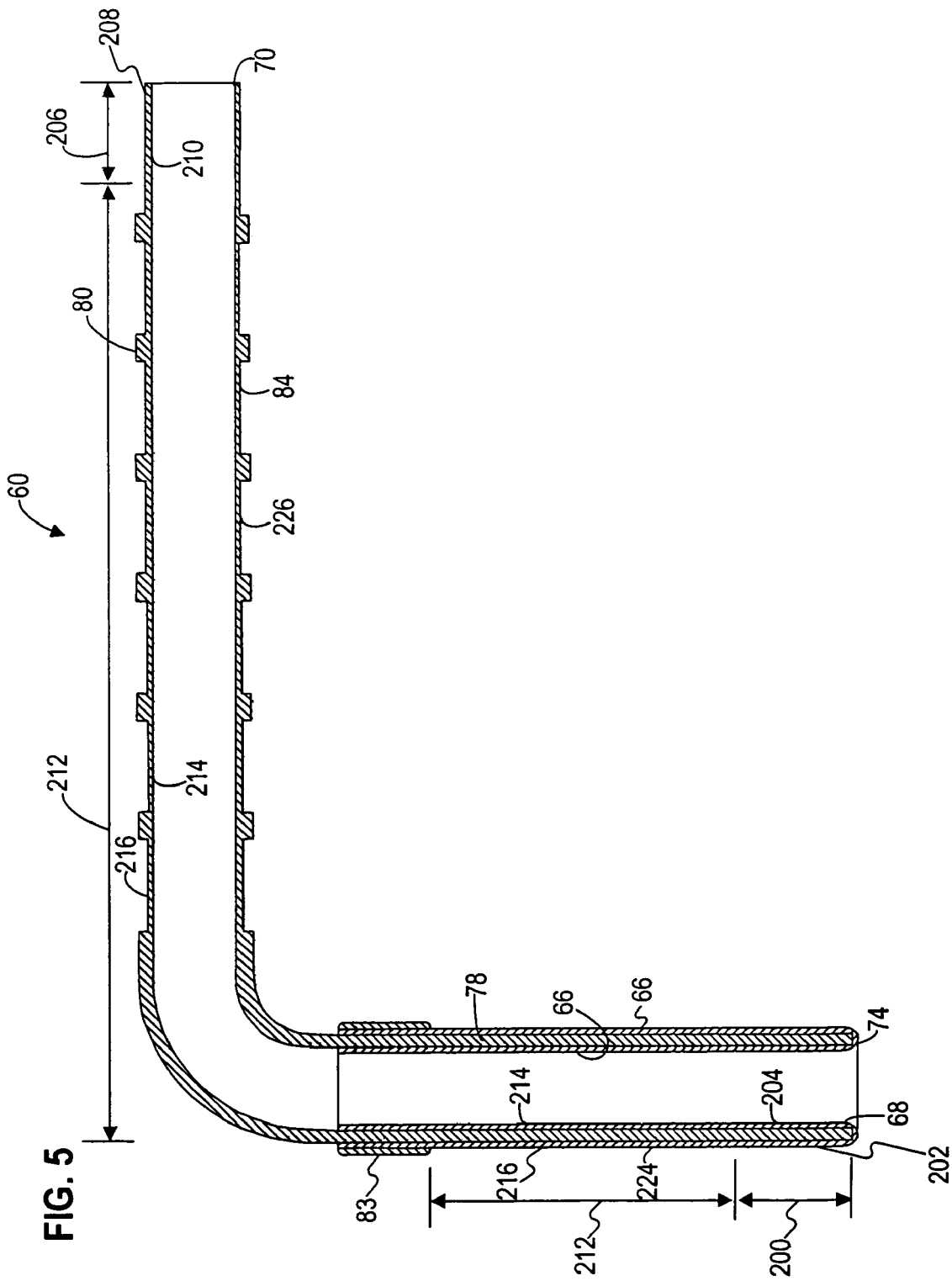
FIG. 5 is an enlarged, cross-sectional view of the implant shown in FIG. 4 and depicting zones for the application of therapeutic agents.

Attention is next directed to the implant 60 shown in FIGS. 4 and 5. The mid zone 212 in FIG. 5 includes a first sub mid zone 224, corresponding to the myocardium portion 78 of the implant 60, and a second sub mid zone 226 corresponding to the vessel portion 84. Table 2, below, provides examples of useful therapeutic agents and the particular locations for the implant 60.

In general, in some applications, it is advantageous in having the inner surface and the outer surface of the vasculature portion 84 be treated with the same therapeutic agent. For example, in some applications, it is advantageous to have both the inner surface and the outer surface of the vasculature portion 84 be coated with an antibiotic. In some applications, in the myocardial portion 78, it may be advantageous to use different type of therapeutic agents on the outer surface than is used on the inner surface. In the interior inlet zone 204, in some implementations, it is useful to have more than one therapeutic agent used. Alternatively, a series of therapeutic agents designed to be released in a series can be helpful.

TABLE 1

Implant 10

| Zone | Therapeutic Agent | Example therapeutic Agent | Useful dimension of zone |
|---|---|---|---|
| exterior inlet 202 | antithrombotic anti-inflammatory anti-proliferative | Streptokinase; Tpa; urokinase; NSAIDS; steroids; paclitaxel (taxol); sirolimus; napamycin; actinomycinD; antigrowth factor antibodies (e.g. antiPDGF antibody); radiation therapy (λ or β); nitric oxide. | 0.25–0.5 in., e.g., 0.3–0.4 in. |
| interior inlet 204 | antithrombotic anti-inflammatory anti-proliferative antibiotic | Streptokinase; Tpa; urokinase; NSAIDS; steroids; paclitaxel (taxol); sirolimus; napamycin; actinomycinD; antigrowth factor antibodies (e.g. antiPDGF antibody); radiation therapy (λ or β); nitric oxide; silver; silver combined with Pb, Pt, Au; silver oxide; heavy metals; vancomycin; rifampin | 0.25–0.5 in., e.g., 0.3–0.4 in. |
| exterior outlet 208 | antithrombotic anti-inflammatory anti-proliferative anti-coagulant anti-platelet | Streptokinase; Tpa; urokinase; NSAIDS; steroids; paclitaxel (taxol); sirolimus; napamycin; actinomycinD; antigrowth factor antibodies (e.g. antiPDGF antibody); radiation therapy (λ or β); nitric oxide; heparin; low MW heparin, hirudin; mitric acid; hirulog; annexim II; aspirin, iclopidine; clopidogrel; dipyridamole; gpIIbIIIa antibodies; and nitric oxide | 0.1–0.4 in., e.g., 0.25–0.35 in. |
| interior outlet 210 | antithrombotic anti-inflammatory anti-proliferative anti-coagulant anti-platelet antibiotic | Streptokinase; Tpa; urokinase; NSAIDS; steroids; paclitaxel (taxol); sirolimus; napamycin; actinomycinD; antigrowth factor antibodies (e.g. antiPDGF antibody); radiation therapy (λ or β); nitric oxide; heparin; low MW heparin, hirudin; mitric acid; hirulog; annexim II; aspirin, iclopidine; clopidogrel; dipyridamole; gpIIbIIIa antibodies; and nitric oxide; silver; silver combined with Pb, Pt, Au; silver oxide; heavy metals; vancomycin; rifampin | 0.1–0.4 in., e.g., 0.25–0.35 in. |
| first sub midzone 220, outer surface | anti-inflammatory angiogenic | NSAIDS; steroids | 0.7–1 in., e.g., 0.85–0.95 in. |
| second sub midzone 222 | untreated | | 0.4–0.8 in., e.g., 0.6–0.7 in. |
| cuff 44 | cell adhesion growth factors | RDG peptides; REDV peptides; laminin; collagen; fibronectin/fibrin; FGF family; PDGF; VEGF; EFG; IGFI II | 0.1–0.5 in., e.g., 0.2–0.3 in. |

TABLE 2

Implant 60

| Zone | Therapeutic Agent | Example therapeutic Agent | Useful dimension of zone |
|---|---|---|---|
| exterior inlet 202 | anti-proliferative anti-inflammatory anti-platelet anti-coagulant | paclitaxel (taxol); sirolimus; napamycin; actinomycinD; antigrowth factor antibodies (e.g. antiPDGF antibody); radiation therapy ($\lambda$ or $\beta$); nitric oxide; NSAIDS; steroids; aspirin, iclopidine; clopidogrel; dipyridamole; gpIIbIIIa antibodies; nitric oxide; heparin; low MW heparin, hirudin; mitric acid; hirulog; annexim II; | 0.25–0.5 in., e.g., 0.3–0.4 in. |
| interior inlet 204 | anti-proliferative anti-inflammatory anti-platelet anti-coagulant | paclitaxel (taxol); sirolimus; napamycin; actinomycinD; antigrowth factor antibodies (e.g. antiPDGF antibody); radiation therapy ($\lambda$ or $\beta$); nitric oxide; NSAIDS; steroids; aspirin, iclopidine; clopidogrel; dipyridamole; gpIIbIIIa antibodies; nitric oxide; heparin; low MW heparin, hirudin; mitric acid; hirulog; annexim II; | 0.25–0.5 in., e.g., 0.3–0.4 in. |
| exterior outlet 208 | antithrombotic anti-proliferative antibiotic anti-coagulant anti-platelet hormone | Streptokinase; Tpa; urokinase; paclitaxel (taxol); sirolimus; napamycin; actinomycinD; antigrowth factor antibodies (e.g. antiPDGF antibody); radiation therapy ($\lambda$ or $\beta$); nitric oxide; silver; silver combined with Pb, Pt, Au; silver oxide; heavy metals; vancomycin; rifampin; heparin; low MW heparin, hirudin; mitric acid; hirulog; annexim II; aspirin, iclopidine; clopidogrel; dipyridamole; gpIIbIIIa antibodies; nitric oxide; estrogen | 0.1–0.4 in., e.g., 0.25–0.35 in. |
| interior outlet 210 | antithrombotic anti-proliferative antibiotic anti-coagulant anti-platelet hormone | Streptokinase; Tpa; urokinase; paclitaxel (taxol); sirolimus; napamycin; actinomycinD; antigrowth factor antibodies (e.g. antiPDGF antibody); radiation therapy ($\lambda$ or $\beta$); nitric oxide; silver; silver combined with Pb, Pt, Au; silver oxide; heavy metals; vancomycin; rifampin; heparin; low MW heparin, hirudin; mitric acid; hirulog; annexim II; aspirin, iclopidine; clopidogrel; dipyridamole; gpIIbIIIa antibodies; nitric oxide; estrogen | 0.1–0.4 in., e.g., 0.25–0.35 in. |
| first sub midzone 224 | untreated | | 0.7–1 in., e.g., 0.85–0.95 in. |
| second sub midzone 226 | antibiotics | silver; silver combined with Pb, Pt, Au; silver oxide; heavy metals; vancomycin; rifampin | 2.5–4.5 in., e.g., 3–4 in. |
| cuff | cell adhesion growth factors | RDG peptides; REDV peptides; laminin; collagen; fibronectin/fibrin; FGF family; PDGF; VEGF; EFG; IGFI II | 0.1–0.5 in., e.g., 0.2–0.3 in. |

Figure 6:
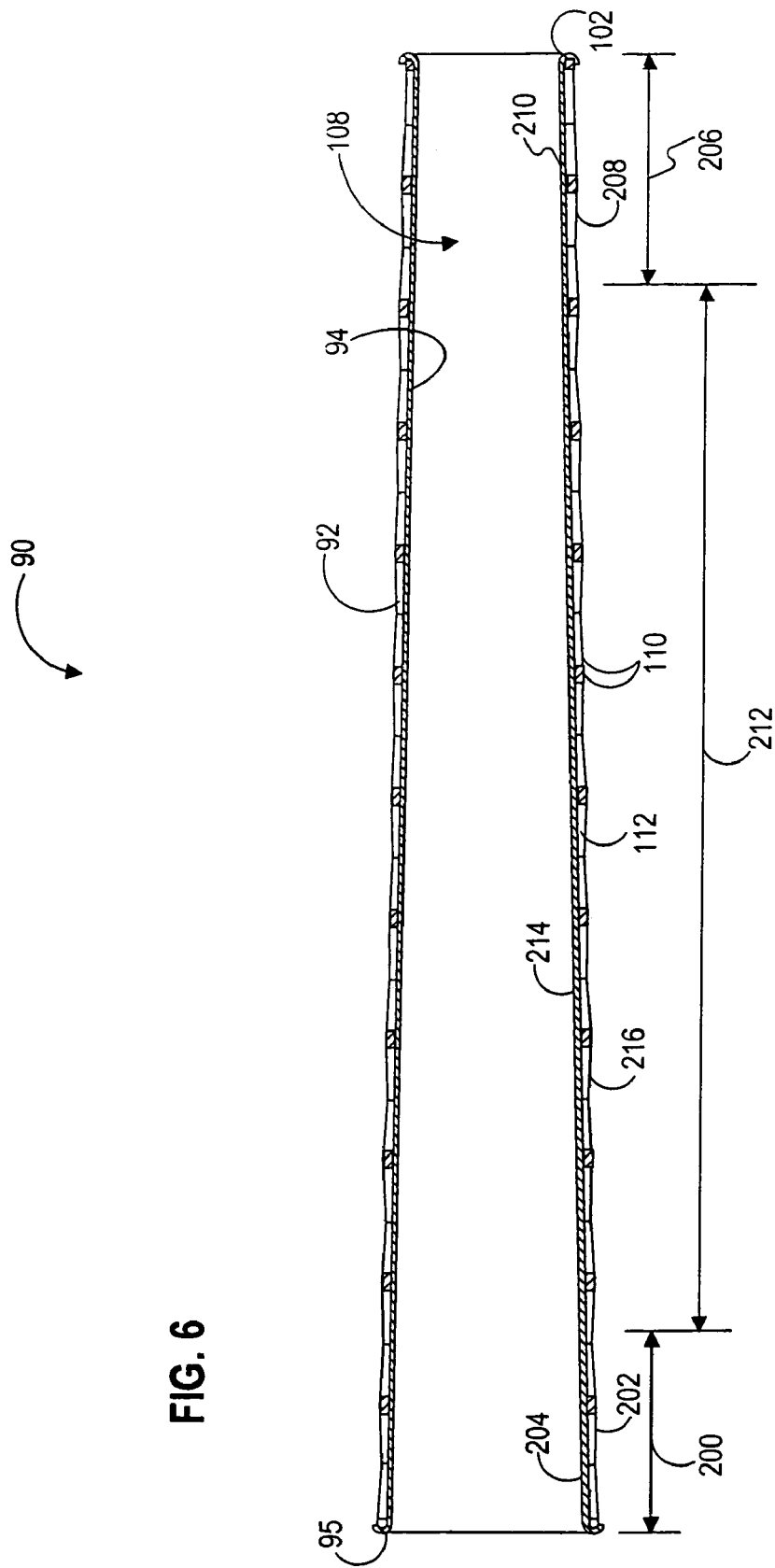
FIG. 6 is an enlarged, cross-sectional view of the implant shown in FIG. 2 and depicting zones for the application of therapeutic agents.

Turning now to the implant 90 illustrated in FIGS. 2 and 6, Table 3 provides example therapeutic agents and particular areas for their application, which may be useful.

In the implant 90, in some embodiments, it is desirable to have a difference in the types of therapeutic agents used on the outer surface than are used in the inner surface. For example, in many embodiments of the implant 90, there will be an antithrombotic agent on the outer surface, but some other agent other than an antithrombotic agent on the inner surface.

TABLE 3

Implant 90

| Zone | Therapeutic Agent | Example therapeutic Agent | Useful dimension of zone |
|---|---|---|---|
| exterior inlet 202 | anti-proliferative anti-inflammatory anti-thrombotic | paclitaxel (taxol); sirolimus; napamycin; actinomycinD; antigrowth factor antibodies (e.g. antiPDGF antibody); radiation therapy (λ or β); nitric oxide; NSAIDS; steroids; Streptokinase; Tpa; urokinase; paclitaxel (taxol); sirolimus; napamycin; actinomycinD; antigrowth factor antibodies (e.g. antiPDGF antibody); radiation therapy (λ or β); nitric oxide | 0.25–0.5 in., e.g., 0.35–0.45 in. |
| interior inlet 204 | anti-proliferative anti-inflammatory anti-thrombotic | paclitaxel (taxol); sirolimus; napamycin; actinomycinD; antigrowth factor antibodies (e.g. antiPDGF antibody); radiation therapy (λ or β); nitric oxide; NSAIDS; steroids; Streptokinase; Tpa; urokinase; paclitaxel (taxol); sirolimus; napamycin; actinomycinD; antigrowth factor antibodies (e.g. antiPDGF antibody); radiation therapy (λ or β); nitric oxide | 0.25–0.5 in., e.g., 0.35–0.45 in. |
| exterior outlet 208 | anti-proliferative anti-inflammatory anti-thrombotic | paclitaxel (taxol); sirolimus; napamycin; actinomycinD; antigrowth factor antibodies (e.g. antiPDGF antibody); radiation therapy (λ or β); nitric oxide; NSAIDS; steroids; Streptokinase; Tpa; urokinase; paclitaxel (taxol); sirolimus; napamycin; actinomycinD; antigrowth factor antibodies (e.g. antiPDGF antibody); radiation therapy (λ or β); nitric oxide | 0.05–0.3 in., e.g., 0.1–0.2 in. |
| interior outlet 210 | anti-proliferative anti-inflammatory anti-thrombotic antibiotic cell seeding | paclitaxel (taxol); sirolimus; napamycin; actinomycinD; antigrowth factor antibodies (e.g. antiPDGF antibody); radiation therapy (λ or β); nitric oxide; NSAIDS; steroids; Streptokinase; Tpa; urokinase; paclitaxel (taxol); sirolimus; napamycin; actinomycinD; antigrowth factor antibodies (e.g. antiPDGF antibody); radiation therapy (λ or β); nitric oxide; silver; silver combined with Pb, Pt, Au; silver oxide; heavy metals; vancomycin; rifampin; endothelium treatment | 0.05–0.3 in., e.g., 0.1–0.2 in. |
| midzone 212, outer surface | anti-inflammatory anti-thrombotic | NSAIDS; steroids; Streptokinase; Tpa; urokinase; paclitaxel (taxol); sirolimus; napamycin; actinomycinD; antigrowth factor antibodies (e.g. antiPDGF antibody); radiation therapy (λ or β); nitric oxide | 1–2 in., e.g., 1.2–1.5 in. |

E. Methods of Making Cardiac Implants

Cardiac implants of the type described herein can be made by, first, providing a scaffold of the type described in connection with the implants 10, 60, 90 defining an open interior volume, an open first end, and an opposite open second end. The method includes covering at least a first portion of the scaffold with a first therapeutic agent, and covering at least a second portion of the scaffold, different from the first portion, with a second therapeutic agent different from the first therapeutic agent. This can include covering: (i) a portion of the inlet zone 200 with one type of therapeutic agent or drug; (ii) a portion of the outlet zone 206 with a different type of therapeutic agent; or (iii) a portion of the mid-zone 212 with a different type of therapeutic agent.

The step of covering at least a first portion can include covering an interior surface adjacent to the open first end with the first therapeutic agent. In the examples described above, the interior surface adjacent to the first open end corresponds to the interior inlet zone 264. As described above, it can be useful to apply therapeutic agents of the type including rhestonsis preventing agents, antithrombotic agents, antibiotic agents, antiproliferative agents, antiplatelet agents, anticoagulant agents, hormones, and combinations thereof.

The step of covering at least a first portion may also include covering an exterior surface adjacent to the first open end with the first therapeutic agent. In the examples described above, this would correspond to applying a therapeutic agent to the exterior inlet zone 202. As described above, it can be helpful to apply the following types of therapeutic agents to the exterior inlet zone 202: antithrombotic agents, antiproliferative agents, anti-inflammatory agents, antiplatelet agents, anticoagulant agents, and combinations thereof The step of covering at least a second portion can include covering an interior surface adjacent to the second open end. In the examples described above, this would correspond to applying a therapeutic agent to the exterior inlet zone 210. Such therapeutic agents can include: rhestenosis preventing agents, antibiotic agents, antiproliferative agents, antiplatelet agents, anticoagulant agents, hormones, and combinations thereof.

In addition, the step of covering at least a second portion can include covering an exterior surface adjacent to the open second end. In the examples above, this would correspond to applying a therapeutic agent to the exterior outlet zone 208. Useful therapeutic agents on the exterior outlet zones 208 include: antithrombotic agents, anti-inflammatory agents, antiproliferative agents, anticoagulant agents, antiplatelet agents, hormones, and combinations thereof.

In some methods, there includes a further step of applying a third therapeutic agent to a third portion of the scaffold, different from the first and second portions. The third therapeutic agent can be different or the same as one of the first and second therapeutic agents. In the examples above, this can include application of a therapeutic agent to a region along the mid zone 212. Useful therapeutic agents along the mid zone 212 include: anti-inflammatory agents, angiogenic agents, antithrombotic agents, antibiotic agents, and combinations thereof.

The step of providing a scaffold can include providing an L-shaped scaffold, of the type illustrated in FIGS. 1, 3, 4, and 5. In other embodiments, the step of providing a scaffold can include providing a straight, bend-free scaffold, of the type shown in FIGS. 2 and 6.

There are several recognized methods for applying the active drug to the inflow zone and/or the outflow zone. Such methods include applying a coating of the drug to the surface of the designated zone. Some of these are described in U.S. Pat. No. 5,697,967; U.S. Pat. No. 6,231,600; and U.S. Pat. No. 6,120,536, each of which is incorporated by reference herein.

The following are some example methods or modes for delivery of the therapeutic agent on the implant 10, 60, 90: fixing a first substance to the scaffold and binding the therapeutic agent to the first substance; applying a polymeric material with the therapeutic agent attached thereto; coating the scaffold with the therapeutic agent as a dissolved solvent; weaving or knitting a fiber containing the therapeutic agent therein; applying a biodegradable material incorporating and releasing the therapeutic agent; providing a sleeve catheter with the therapeutic agent in the lumen; forming the therapeutic agent as a temporary stent that dissolves; compressing the therapeutic agent into pores of the scaffold; or providing a permeable membrane with the therapeutic agent transported through the membrane.

F. Methods of Use

The implants 10, 60, 90 can be used to treat humans. In one application, the implant 10, 60, 90 can be used in a method for performing a coronary vessel bypass procedure. This method includes forming a blood flow path, such as pathway 42 (FIG. 1) or pathway 109 (FIG. 2) from the heart chamber 38, 106 directly to the coronary vessel 36, 98 at a site in the vessel positioned between an obstruction in the vessel and tissue of the heart to be supplied with blood by the vessel. This step includes placing the implant 10, 60, 90 in the heart wall 32, 104 between the heart chamber 38, 105 and the vessel 36, 98 with one end of the implant 10, 60, 90 protruding into the heart chamber 38, 106 beyond an interior surface of the myocardium 32, 104. The method includes the implant 10, 60, 90 including a first therapeutic agent in covering relation to at least a first portion and a second therapeutic agent in covering relation to at least a second portion of the implant.

As described above, the first portion can be one of the inlet zone 200, outlet zone 206, and mid zone 212; while the second portion can be one of the inlet zone 200, the outlet zones 206, and the mid zone 212. As described above, the therapeutic agents can be applied to exterior portions, interior portions, or both, along the conduit or scaffold. Use of therapeutic agents in selected, strategic positions can help the healing the process and improve the health of the patient, as described above.

What is claimed is:

1. A cardiac implant comprising:
   (a) a scaffold defining an open interior volume, an open first end, and an opposite open second end;
      (i) said open interior volume comprising a blood flow conduit to direct blood flow through the scaffold including through the open first end and the open second end;
      (ii) said scaffold having an exterior surface and an opposite, interior surface;
         (A) said interior surface lining said open, interior volume;
   (b) a first therapeutic agent in at least partial covering relation to at least a first portion of one of said exterior surface and said interior surface; and
   (c) a second therapeutic agent, different from said first therapeutic agent, in at least partial covering relation to at least a second portion of one of said exterior surface and said interior surface,
   wherein said first therapeutic agent is not in covering relation to the second portion.

2. An implant according to claim 1 wherein:
   (a) said first therapeutic agent comprises one of a therapeutic agent selected from the group consisting essentially of: anti-thrombotic agents, anti-inflamatory agents, anti-proliferative agents, antibiotic agents, angiogenic agents, anti-platelet agents, anti-coagulant agents, restenosis preventing agents, hormones, and combinations thereof.

3. An implant according to claim 2 wherein:
   (a) said second therapeutic agent comprises one of a therapeutic agent selected from the group consisting essentially of: anti-thrombotic, anti-inflamatory, anti-proliferative, antibiotics, angiogenic, anti-platelet agents, anti-coagulant agents, hormones, and combinations thereof.

4. An implant according to claim 1 wherein:
   (a) said first therapeutic agent is in covering relation to selected zones on at least one of said exterior surface and said interior surface.

5. An implant according to claim 4 wherein:
   (a) said second therapeutic agent is in covering relation to selected zones, at locations different from said first therapeutic agent, on at least one of said exterior surface and said interior surface.

6. An implant according to claim 5 wherein:
(a) said open first end comprises a blood inflow end;
(b) said first selected zones includes an inlet zone on at least one of said exterior surface and said interior surface adjacent to said blood inflow end; and
(c) one of said first therapeutic agent and said second therapeutic agent is in covering relation to said inlet zone.

7. An implant according to claim 6 wherein:
(a) said inlet zone extends from said open first end along said scaffold a distance no greater than 0.5 inch.

8. An implant according to claim 7 wherein:
(a) said open second end comprises a blood outflow end;
(b) said selected zones includes an outlet zone on at least one of said exterior surface and said interior surface adjacent to said blood outflow end; and
(c) one of said first therapeutic agent and said second therapeutic agent is in covering relation to said outlet zone.

9. An implant according to claim 8 wherein:
(a) said outlet zone extends from said open second end along said scaffold a distance no greater than 3.75 inches.

10. An implant according to claim 9 wherein:
(a) said inlet zone includes an inlet exterior zone on said exterior surface and an inlet interior zone on said interior surface.

11. An implant according to claim 10 wherein:
(a) said outlet zone includes an outlet exterior zone on said exterior surface and an outlet interior zone on said interior surface.

12. An implant according to claim 11 wherein:
(a) said selected zones includes at least one mid-zone between said inlet zone and said outlet zone.

13. An implant according to claim 12 wherein:
(a) said mid-zone includes a plurality of mid-zones between said inlet zone and said outlet zone.

14. An implant according to claim 12 wherein:
(a) said mid-zone includes a mid-exterior zone on said exterior surface and a mid-interior zone on said interior surface.

15. An implant according to claim 11 wherein:
(a) said inlet exterior zone is at least partially covered with one of said first therapeutic agent and said second therapeutic agent comprising one from the group consisting essentially of: antiproliferative agents, anti-inflamatory agents, anti-platelet agents, anti-coagulant agents, and combinations thereof.

16. An implant according to claim 15 wherein:
(a) said antiproliferative agents include at least one of: paclitaxel; taxol; sirolimus; napamycin; actinomycinD; anti PDGF antibodies; .lambda.or .beta.radiation; and nitric oxide;
(b) said anti-inflamatory agents include at least one of: non-steroids and steroids;
(c) said anti-platelet agents include at least one of: aspirin, iclopidine; clopidogrel; dipyridamole; gpIIbIIIa antibodies; and nitric oxide; and (d) said anti-coagulant agents include at least one of: heparin; low MW heparin, hirudin; mitric acid; hirulog; and annexim II.

17. An implant according to claim 11 wherein:
(a) said inlet interior zone is at least partially covered with one of said first therapeutic agent and said second therapeutic agent comprising one from the group consisting essentially of: antiproliferative agents, anti-inflamatory agents, anti-platelet agents, anti-coagulant agents, and combinations thereof.

18. An implant according to claim 17 wherein:
(a) said antiproliferative agents include at least one of: paclitaxel; taxol; sirolimus; napamycin; actinomycinD; anti PDGF antibodies; .lambda.or .beta. radiation; and nitric oxide;
(b) said anti-inflamatory agents include at least one of: non-steroids and steroids;
(c) said anti-platelet agents include at least one of: aspirin, iclopidine; clopidogrel; dipyridamole; gpIIbIIIa antibodies; and nitric oxide; (d) said anti-coagulant agents include at least one of: heparin; low MW heparin, hirudin; mitric acid; hirulog; and annexim II.

19. An implant according to claim 11 wherein:
(a) said outlet interior zone is at least partially covered with one of said first therapeutic agent and said second therapeutic agent comprising one from the group consisting essentially of: restenosis preventing agents, anti-thrombotic agents, anti-biotic agents, antiproliferative agents, anti-platelet agents, anti-coagulant agents, hormones, and combinations thereof.

20. An implant according to claim 17 wherein:
(a) said antithrombotic agents include at least one of: streptokinase; Tpa; and urokinase;
(b) said antibiotic agents include at least one of: silver; silver combined with Pb, Pt, Au; silver oxide; heavy metals; vancomycin; and rifampin;
(c) said antiproliferative agents include at least one of: paclitaxel; taxol; sirolimus; napamycin; actinomycinD; anti PDGF antibodies; .lambda.or .beta.radiation; and nitric oxide;
(d) said anti-platelet agents include at least one of: aspirin, iclopidine; clopidogrel; dipyridamole; gpIIbIIIa antibodies; and nitric oxide;
(e) said anti-coagulant agents include at least one of: heparin; low MW heparin, hirudin; mitric acid; hirulog; and annexim II; and
(f) said hormones includes at least one of: estrogen.

21. An implant according to claim 11 wherein:
(a) said outlet exterior zone is at least partially covered with one of said first therapeutic agent and said second therapeutic agent comprising one from the group consisting essentially of: anti-thrombotic agents, anti-biotic agents, antiproliferative agents, anti-platelet agents, anti-coagulant agents, hormones, and combinations thereof.

22. An implant according to claim 21 wherein:
(a) said antithrombotic agents include at least one of: streptokinase; Tpa; and urokinase;
(b) said antibiotic agents include at least one of: silver; silver combined with Pb, Pt, Au; silver oxide; heavy metals; vancomycin; and rifampin;
(c) said antiproliferative agents include at least one of: paclitaxel; taxol; sirolimus; napamycin; actinomycinD; anti PDGF antibodies; .lambda.or .beta. radiation; and nitric oxide;
(d) said anti-platelet agents include at least one of: aspirin, iclopidine; clopidogrel; dipyridamole; gpIIbIIIa antibodies; and nitric oxide;
(e) said anti-coagulant agents include at least one of: heparin; low MW heparin, hirudin; mitric acid; hirulog; and annexim II; and
(f) said hormones includes at least one of: estrogen.

23. An implant according to claim 11 wherein: (a) said scaffold is L-shaped.

24. An implant according to claim 23 wherein:
(a) said scaffold defines a first portion dimensioned to extend through a myocardium and into a heart chamber, and a second portion dimensioned to be in blood flow communication with a coronary vasculature;
(i) said first portion defining said open first end; and
(ii) said second portion defining said open second end.

25. An implant according to claim 24 further including:
(a) a cuff circumscribing a section of said first portion; said cuff including at least one of cell adhesion agents and growth agents.

26. An implant according to claim 24 wherein:
(a) said second portion includes a permeable mesh section defining said open second end.

27. An implant according to claim 24 wherein:
(a) said scaffold includes a plurality of rings circumscribing at least a partial section of said second portion.

28. An implant according to claim 11 wherein:
(a) said scaffold is straight and bend-free between said open first end and said open second end.

29. An implant according to claim 28 wherein:
(a) said scaffold is tapered between said open first end and said open second end at an angle of between 0.05–0.25.degree.

30. An implant according to claim 28 wherein:
(a) said scaffold further includes a covering thereon.

31. A method for making a cardiac implant for establishing a blood flow path through a myocardium between a heart chamber and a lumen of a coronary vessel residing at an exterior of the myocardium; the method comprising:
(a) providing a scaffold defining an open interior volume, an open first end, and an opposite open second end;
(b) covering at least a first portion of the scaffold with a first therapeutic agent, and
(c) covering at least a second portion of the scaffold with a second therapeutic agent, different from the first therapeutic agent,
wherein said first therapeutic agent does not cover the second portion.

32. A method according to claim 31 wherein:
(a) said step of covering at least a first portion includes covering an interior surface adjacent to said open first end with a first therapeutic agent including one from the group consisting essentially of: anti-thrombotic agents, anti-biotic agents, antiproliferative agents, anti-platelet agents, anti-coagulant agents, hormones, and combinations thereof.

33. A method according to claim 32 wherein:
(a) said step of covering at least a first portion includes covering an exterior surface adjacent to the open first end with the first therapeutic agent.

34. A method according to claim 33 wherein:
(a) said step of covering at least a second portion includes covering an interior surface adjacent to said open second end with a second therapeutic agent including one form the group consisting essentially of: anti-thrombotic agents, anti-biotic agents, antiproliferative agents, anti-platelet agents, anti-coagulant agents, hormones, and combinations thereof.

35. A method according to claim 34 wherein:
(a) said step of covering at least a second portion includes covering an exterior surface adjacent to the open second end with the second therapeutic agent.

36. A method according to claim 31 wherein:
(a) said step of providing a scaffold includes providing an L-shaped scaffold.

37. A method according to claim 31 wherein:
(a) said step of providing a scaffold includes providing a straight, bend-free scaffold.

38. A method for performing a coronary vessel bypass procedure for supplementing a flow of blood to a coronary vessel; the method comprising:
(a) forming a blood flow path from a heart chamber directly to the coronary vessel at a site in the vessel positioned between an obstruction in the vessel and tissue of the heart to be supplied with blood by the vessel;
(i) the forming including placing a conduit in a heart wall between the chamber and the vessel with a first end of the conduit protruding into the chamber and protruding beyond an interior surface of the heart wall;
(ii) the conduit including a first therapeutic agent in covering relation to at least a first portion and a second therapeutic agent in covering relation to at least a second portion,
wherein the first therapeutic agent is not in covering relation to the second portion.

* * * * *

UNITED STATES PATENT AND TRADEMARK OFFICE
CERTIFICATE OF CORRECTION

PATENT NO. : 7,008,397 B2
APPLICATION NO. : 10/075518
DATED : March 7, 2006
INVENTOR(S) : Katherine S. Tweden It is certified that error appears in the above-identified patent and that said Letters Patent is hereby corrected as shown below:

In claim 16, column 19, line 52; claim 18, column 20, line 4; and claim 22, column 20, line 54, ".lambda.or .beta." should read --ë or â---.

In claim 34, column 22, line 9, "form" should read --from--.

Signed and Sealed this

Fifth Day of February, 2008

JON W. DUDAS
*Director of the United States Patent and Trademark Office*